(12) United States Patent
De Taboada et al.

(10) Patent No.: US 10,653,889 B2
(45) Date of Patent: May 19, 2020

(54) METHOD FOR PROVIDING PHOTOTHERAPY TO THE BRAIN

(75) Inventors: Luis De Taboada, Carlsbad, CA (US); Jackson Streeter, Reno, NV (US)

(73) Assignee: Pthera LLC, Newark, DE (US)

(*) Notice: Subject to any disclaimer, the term of this patent is extended or adjusted under 35 U.S.C. 154(b) by 2365 days.

(21) Appl. No.: 12/561,231

(22) Filed: Sep. 16, 2009

(65) Prior Publication Data

US 2010/0010592 A1    Jan. 14, 2010

Related U.S. Application Data

(63) Continuation of application No. 10/938,423, filed on Sep. 10, 2004, now abandoned, which is a (Continued)

(51) Int. Cl.
*A61N 5/06* (2006.01)
*A61N 5/067* (2006.01)
(Continued)

(52) U.S. Cl.
CPC ......... *A61N 5/0613* (2013.01); *A61N 5/0622* (2013.01); *A61N 1/40* (2013.01); (Continued)

(58) Field of Classification Search
CPC .. A61N 5/0613; A61N 5/0617; A61N 5/0622; A61N 1/40; A61N 2005/067; A61N 2005/007; A61N 2005/0647; A61N 2005/0652; A61N 2005/0659; A61N 7/00; A61B 5/4064; A61B 5/4836; (Continued)

(56) References Cited

U.S. PATENT DOCUMENTS 5,595,568 A * 1/1997 Anderson ............ A61B 18/203
606/9
5,603,728 A * 2/1997 Pachys ...................... A61F 7/02
607/104

(Continued)

FOREIGN PATENT DOCUMENTS

EP       2082696 A1      7/2009
WO    WO 99/62599    * 12/1999 ..... A61N 2005/0659
(Continued)

OTHER PUBLICATIONS

Mochizuki-oda et al "Effects of near-infra-red laser irradiation on adenosine triphosphate and adenosine diphosphate contents of rat brain tissue", Neurosci Lett, vol. 323, 2002, pp. 207-210.*

(Continued)

*Primary Examiner* — John R Downey
(74) *Attorney, Agent, or Firm* — Fish & Richardson P.C.

(57) ABSTRACT

Methods for providing and/or determining therapeutic treatment of at least a portion of a patient's brain are provided. The method includes applying light to at least a portion of a patient's brain and monitoring at least one physiological parameter of the patient. The method further includes receiving real-time feedback information regarding the at least one monitored physiological parameter and adjusting a treatment parameter of the applied light based on the real-time feedback information.

25 Claims, 20 Drawing Sheets

Related U.S. Application Data continuation-in-part of application No. 10/682,379, filed on Oct. 9, 2003, now Pat. No. 7,303,578, which is a continuation-in-part of application No. 10/287,432, filed on Nov. 1, 2002, now abandoned.

(60) Provisional application No. 60/502,147, filed on Sep. 11, 2003, provisional application No. 60/487,979, filed on Jul. 17, 2003, provisional application No. 60/442,693, filed on Jan. 24, 2003, provisional application No. 60/369,260, filed on Apr. 2, 2002, provisional application No. 60/336,436, filed on Nov. 1, 2001, provisional application No. 60/585,055, filed on Jul. 2, 2004.

(51) Int. Cl.
*A61N 5/00* (2006.01)
*A61N 7/00* (2006.01)
*A61N 1/40* (2006.01)

(52) U.S. Cl.
CPC .............. *A61N 5/0617* (2013.01); *A61N 7/00* (2013.01); *A61N 2005/007* (2013.01); *A61N 2005/067* (2013.01); *A61N 2005/0647* (2013.01); *A61N 2005/0652* (2013.01); *A61N 2005/0659* (2013.01)

(58) Field of Classification Search
CPC ... A61B 5/4082; A61B 5/4088; A61B 5/4094; A61B 2017/00057–00092; A61B 2018/00446; A61B 2018/00636–00654; A61B 18/203; A61B 18/2018; A61B 18/00452; A61B 18/00476
USPC .......................................... 607/88–90; 606/9
See application file for complete search history.

(56) References Cited

U.S. PATENT DOCUMENTS

| | | | |
|---|---|---|---|
| 5,617,258 A | 4/1997 | Negus et al. | |
| 5,810,801 A | 9/1998 | Anderson et al. | |
| 5,820,626 A * | 10/1998 | Baumgardner | A61B 18/00 606/13 |
| 6,015,404 A * | 1/2000 | Altshuler | A61B 18/203 606/10 |
| 6,059,820 A * | 5/2000 | Baronov | A61B 18/0218 607/89 |
| 6,366,802 B1 * | 4/2002 | Haber | A61N 5/0619 607/88 |
| 6,514,278 B1 | 2/2003 | Hibst | |
| 7,217,266 B2 * | 5/2007 | Anderson | A61B 5/0059 606/10 |
| 7,303,578 B2 * | 12/2007 | De Taboada | A61N 5/0613 607/89 |
| 7,575,589 B2 | 8/2009 | DeTaboada et al. | |
| 2004/0030325 A1 | 2/2004 | Cahir et al. | |
| 2006/0155266 A1 * | 7/2006 | Manstein | A61B 18/203 606/17 |
| 2007/0255355 A1 * | 11/2007 | Altshuler | A61B 18/203 607/86 |
| 2007/0255359 A1 * | 11/2007 | Neev | A61N 5/0613 607/90 |
| 2011/0032960 A1 * | 2/2011 | Gerlitz | A61N 5/0616 372/29.021 |
| 2011/0190745 A1 * | 8/2011 | Uebelhoer | A61B 18/203 606/9 |

FOREIGN PATENT DOCUMENTS

| | | |
|---|---|---|
| WO | WO1999061105 | 12/1999 |
| WO | WO 00/25684 | 5/2000 |
| WO | WO 06/115761 | 11/2006 |
| WO | WO 08/049905 | 5/2008 |

OTHER PUBLICATIONS

Alexander, "Biology of Parkinson's disease—pathogenesis and pathophysiology of a multisystem neurodegenerative disorder", Dialogues Clin Neurosci, vol. 6, No. 3, Sep. 2004, pp. 259-280.*

Lapchack et al "Transcranial Infrared Laser Therapy Improves Clinical Rating Scores After Embolic Strokes in Rabbits", Stroke, vol. 35 Jun. 2004 pp. 1985-1988.*

Rajendran et al, "Imaging Adenosine Triphosphate ATP", Biol Bull., vol. 231, No. 1, Aug. 2016, pp. 73-84.*

EPO Extended Search Report re EP Application No. 09170679.6, dated Jan. 4, 2010. in 6 pages.

Zhang et al., "Characterization of ATP Alternations in an Alzheimer's Transgenic Mouse Model", J. Alzheimers Dis., 2015, 44(2): 375-378, doi:10.3233/JAD-141890.

"Genetics Home Reference—Parkinson disease", U.S. National Library of Medicine, National Institutes of Health, https://ghr.nlm.nih.gov/condition/parkinson-disease, May 2012, pp. 1-11.

Wang et al., "An astroglial basis of major depressive disorder? An overview", Glia. 2017;00:000-000. https://doi.org/10.1002/glia.23143, pp. 1-24.

* cited by examiner

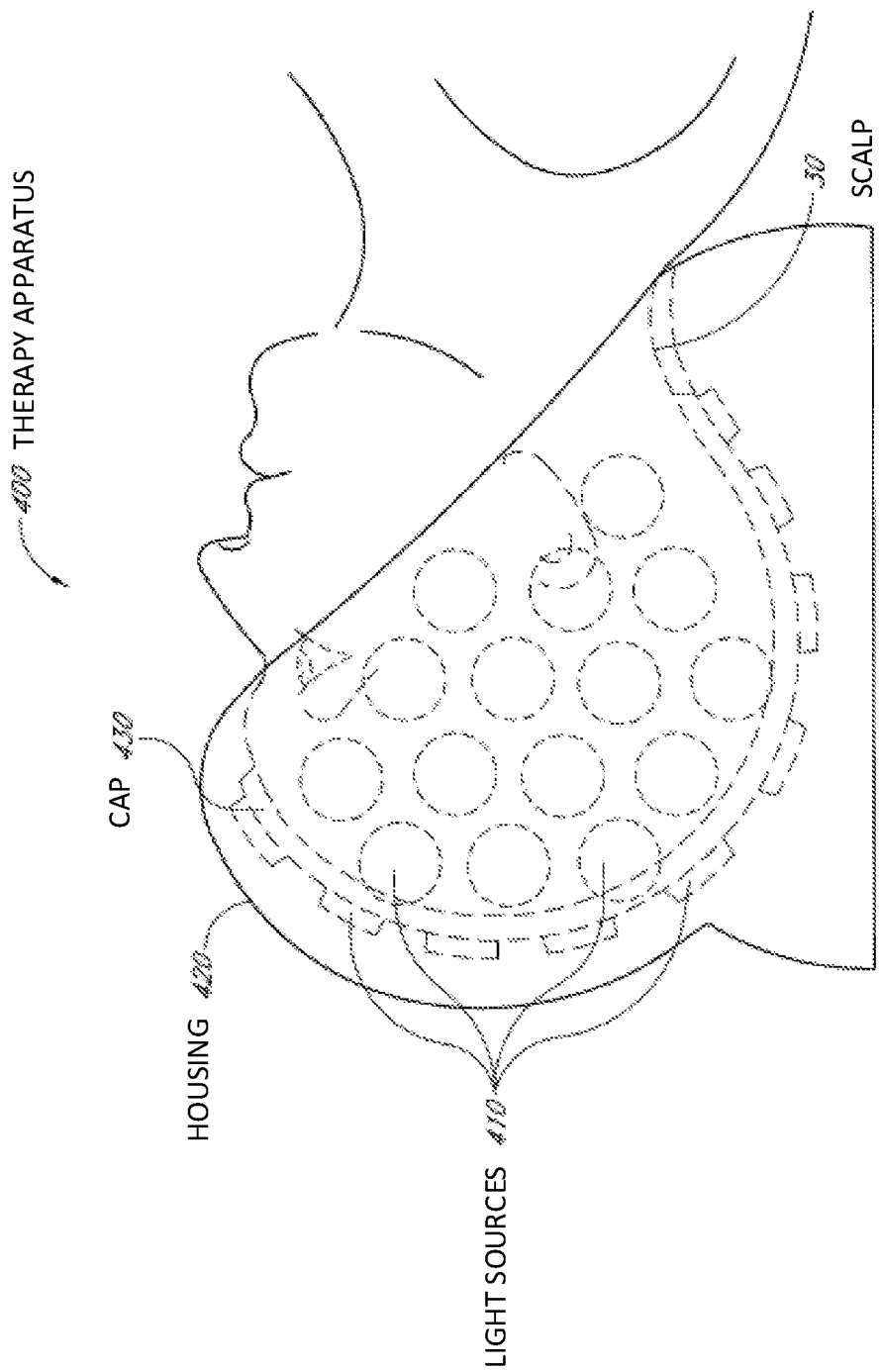

METHOD FOR PROVIDING PHOTOTHERAPY TO THE BRAIN

CLAIM OF PRIORITY

This application is a continuation of, and claims priority under 35 U.S.C. § 120 to, U.S. patent application Ser. No. 10/938,423, filed Sep. 10, 2004, which is a continuation-in-part of, and claims priority under 35 U.S.C. § 120 to, U.S. patent application Ser. No. 10/682,379, filed Oct. 9, 2003 and issued as U.S. Pat. No. 7,303,578 on Dec. 4, 2007, which is a continuation-in-part of, and claims priority under 35 U.S.C. § 120 to, U.S. patent application Ser. No. 10/287,432, filed Nov. 1, 2002. The entirety of each of the above-referenced applications is hereby expressly incorporated by reference herein. U.S. patent application Ser. No. 10/938,423 also claims benefit under 35 U.S.C. § 119(e) to U.S. Provisional Application No. 60/502,147, filed Sep. 11, 2003 and U.S. Provisional Application No. 60/585,055, filed Jul. 2, 2004, both of which are incorporated in their entireties by reference herein. U.S. patent application Ser. No. 10/682,379 also claims benefit under 35 U.S.C. § 119(e) to U.S. Provisional Application No. 60/442,693, filed Jan. 24, 2003, U.S. Provisional Application No. 60/487,979, filed Jul. 17, 2003, and U.S. Provisional Application No. 60/502,147, filed Sep. 11, 2003, each of which is incorporated in its entirety by reference herein. U.S. patent application Ser. No. 10/287,432 also claims benefit under 35 U.S.C. § 119(e) to U.S. Provisional Application No. 60/336,436, filed Nov. 1, 2001 and U.S. Provisional Application No. 60/369,260, filed Apr. 2, 2002, both of which are incorporated in their entireties by reference herein.

BACKGROUND OF THE INVENTION

Field of the Invention

The present invention relates in general to phototherapy, and more particularly, to novel apparatuses and methods for phototherapy of brain tissue affected by stroke.

Description of the Related Art

Stroke, also called cerebrovascular accident (CVA), is a sudden disruption of blood flow to a discrete area of the brain that is brought on by a clot lodging in an artery supplying that area of that brain, or by a cerebral hemorrhage due to a ruptured aneurysm or a burst artery. The consequence of stroke is a loss of function in the affected brain region and concomitant loss of bodily function in areas of the body controlled by the affected brain region. Depending upon the extent and location of the primary insult in the brain, loss of function varies greatly from mild or severe, and may be temporary or permanent. Lifestyle factors such as smoking, diet, level of physical activity and high cholesterol increase the risk of stroke, and thus stroke is a major cause of human suffering in developed nations. Stroke is the third leading cause of death in most developed nations, including the United States.

Until recently, stroke treatment was restricted to providing basic life support at the time of the stroke, followed by rehabilitation. Recently, new drug therapies have taken the approach of breaking up blood clots or protecting surviving at-risk neurons from further damage.

Thrombolytic therapy includes aspirin or intravenous heparin to prevent further clot formation and to maintain blood flow after an ischemic stroke. Thrombolytic drugs include tissue plasminogen activator (TPA) and genetically engineered versions thereof, and streptokinase. However, streptokinase does not appear to improve the patient's outlook unless administered early (within three hours of stroke). TPA when administered early appears to substantially improve prognosis, but slightly increases the risk of death from hemorrhage. In addition, over half of stroke patients arrive at the hospital more than three hours after a stroke, and even if they arrive quickly, a CT scan must first confirm that the stroke is not hemorrhagic, which delays administration of the drug. Also, patients taking aspirin or other blood thinners and patients with clotting abnormalities should not be given TPA.

Neuroprotective drugs target surviving but endangered neurons in a zone of risk surrounding the area of primary infarct. Such drugs are aimed at slowing down or preventing the death of such neurons, to reduce the extent of brain damage. Certain neuroprotective drugs are anti-excitotoxic, i.e., work to block the excitotoxic effects of excitatory amino acids such as glutamate that cause cell membrane damage under certain conditions. Other drugs such as citicoline work by repairing damaged cell membranes. Lazaroids such as Tirilazed (Freedox) counteract oxidative stress produced by oxygen-free radicals produced during stroke. Other drugs for stroke treatment include agents that block the enzyme known as PARP, and calcium-channel blockers such as nimodipine (Nimotop) that relax the blood vessels to prevent vascular spasms that further limit blood supply. However, the effect of nimodipine is reduced if administered beyond six hours after a stroke and it is not useful for ischemic stroke. In addition, drug therapy includes the risk of adverse side effects and immune responses.

Surgical treatment for stroke includes carotid endarterectomy, which appears to be especially effective for reducing the risk of stroke recurrence for patients exhibiting arterial narrowing of more than 70%. However, endarterectomy is highly invasive, and risk of stroke recurrence increases temporarily after surgery. Experimental stroke therapies include an angiography-type or angioplasty-type procedure using a thin catheter to remove or reduce the blockage from a clot. However, such procedures have extremely limited availability and increase the risk of embolic stroke. Other surgical interventions, such as those to repair an aneurysm before rupture remain controversial because of disagreement over the relative risks of surgery versus leaving the aneurysm untreated.

Against this background, a high level of interest remains in finding new and improved therapeutic apparatuses and methods for the treatment of stroke. In particular, a need remains for relatively inexpensive and non-invasive approaches to treating stroke that also avoid the limitations of drug therapy.

SUMMARY OF THE INVENTION

One embodiment of the present invention provides a therapy apparatus for treating a patient's brain. The therapy apparatus comprises a light source having an output emission area positioned to irradiate a portion of the brain with an efficacious power density and wavelength of light. The therapy apparatus further comprises an element interposed between the light source and the patient's scalp. The element is adapted to inhibit temperature increases at the scalp caused by the light.

Another embodiment of the present invention provides a therapy apparatus for treating brain tissue. The therapy apparatus comprises a light source positioned to irradiate at least a portion of a patient's head with light. The light has a wavelength and power density which penetrates the cranium to deliver an efficacious amount of light to brain tissue. The therapy apparatus further comprises a material which inhibits temperature increases of the head.

Another embodiment of the present invention provides a therapy apparatus for treating a patient's brain. The therapy apparatus comprises a light source adapted to irradiate at least a portion of the brain with an efficacious power density and wavelength of light. The therapy apparatus further comprises an element adapted to inhibit temperature increases at the scalp. At least a portion of the element is in an optical path of the light from the light source to the scalp.

Another embodiment of the present invention provides a therapy apparatus for treating a patient's brain. The therapy apparatus comprises a light source adapted to irradiate at least a portion of the brain with an efficacious power density and wavelength of light. The therapy apparatus further comprises a controller for energizing said light source so as to selectively produce a plurality of different irradiation patterns on the patient's scalp. Each of said irradiation patterns is comprised of at least one illumination area that is small compared to the patient's scalp, and at least one non-illuminated area.

Another embodiment of the present invention provides a method comprising interposing a head element between a light source and the patient's scalp. The element is comprised of a material which, for an efficacious power density at the brain, inhibits temperature increases at the scalp.

Another embodiment of the present invention provides a therapy apparatus for treating a patient's brain. The therapy apparatus comprises a light source adapted to irradiate at least a portion of the brain with an efficacious power density and wavelength of light. The therapy apparatus further comprises a biomedical sensor configured to provide real-time feedback information. The therapy apparatus further comprises a controller coupled to the light source and the biomedical sensor. The controller is configured to adjust said light source in response to the real-time feedback information.

Another embodiment of the present invention provides a method of treating brain tissue. The method comprises introducing light of an efficacious power density onto brain tissue by directing light through the scalp of a patient. Directing the light comprises providing a sufficiently large spot size on said scalp to reduce the power density at the scalp below the damage threshold of scalp tissue, while producing sufficient optical power at said scalp to achieve said efficacious power density at said brain tissue.

Another embodiment of the present invention provides a method of treating a patient's brain. The method comprises covering at least a significant portion of the patient's scalp with a light-emitting blanket.

Another embodiment of the present invention provides a method of treating a patient's brain following a stroke. The method comprises applying low-level light therapy to the brain no earlier than several hours following said stroke.

Another embodiment of the present invention provides a method for treating a patient's brain. The method comprises introducing light of an efficacious power density onto a target area of the brain by directing light through the scalp of the patient. The light has a plurality of wavelengths and the efficacious power density is at least 0.01 mW/cm$^2$ at the target area.

Another embodiment of the present invention provides a method for treating a patient's brain. The method comprises directing light through the scalp of the patient to a target area of the brain concurrently with applying an electromagnetic field to the brain. The light has an efficacious power density at the target area and the electromagnetic field has an efficacious field strength.

Another embodiment of the present invention provides a method for treating a patient's brain. The method comprises directing an efficacious power density of light through the scalp of the patient to a target area of the brain concurrently with applying an efficacious amount of ultrasonic energy to the brain.

Another embodiment of the present invention provides a method of providing a neuroprotective effect in a patient that had an ischemic event in the brain. The method comprises identifying a patient who has experienced an ischemic event in the brain. The method further comprises estimating the time of the ischemic event. The method further comprises commencing administration of a neuroprotective effective amount of light energy to the brain no less than about two hours following the time of the ischemic event.

Another embodiment of the present invention provides a therapy apparatus for treating a patient's brain. The therapy apparatus comprises a plurality of light sources. Each light source has an output emission area positioned to irradiate a corresponding portion of the brain with an efficacious power density and wavelength of light. The therapy apparatus further comprises an element interposed between the light sources and the patient's scalp. The element inhibits temperature increases at the scalp caused by the light.

Another embodiment of the present invention provides a therapy apparatus for treating brain tissue. The therapy apparatus comprises a plurality of light sources. Each light source is positioned to irradiate at least a corresponding portion of a patient's head with light having a wavelength and power density which penetrates the cranium to deliver an efficacious amount of light to brain tissue. The therapy apparatus further comprises a material which inhibits temperature increases of the head.

Another embodiment of the present invention provides a therapy apparatus for treating a patient's brain. The therapy apparatus comprises a plurality of light sources. Each light source irradiates at least a corresponding portion of the brain with an efficacious power density and wavelength of light. The therapy apparatus further comprises a controller for energizing said light sources so as to selectively produce a predetermined irradiation pattern on the patient's scalp.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 16 schematically illustrates an exemplary therapy apparatus in accordance with embodiments described herein.

DETAILED DESCRIPTION OF THE PREFERRED EMBODIMENT

Low level light therapy ("LLLT") or phototherapy involves therapeutic administration of light energy to a patient at lower power outputs than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. No. 6,537,304 to Oron and U.S. patent application Ser. No. 10/353,130, both of which are incorporated in their entireties by reference herein.)

Laser therapy has been shown to be effective in a variety of settings, including treating lymphoedema and muscular trauma, and carpal tunnel syndrome. Recent studies have shown that laser-generated infrared radiation is able to penetrate various tissues, including the brain, and modify function. In addition, laser-generated infrared radiation can induce angiogenesis, modify growth factor (transforming growth factor-β) signaling pathways, and enhance protein synthesis.

However, absorption of the light energy by intervening tissue can limit the amount of light energy delivered to the target tissue site, while heating the intervening tissue. In addition, scattering of the light energy by intervening tissue can limit the power density or energy density delivered to the target tissue site. Brute force attempts to circumvent these effects by increasing the power and/or power density applied to the outside surface of the body can result in damage (e.g., burning) of the intervening tissue.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found. However, certain embodiments, as described herein, provide devices and methods which can achieve this goal.

Such embodiments may include selecting a wavelength of light at which the absorption by intervening tissue is below a damaging level. Such embodiments may also include setting the power output of the light source at very low, yet efficacious, power densities (e.g., between approximately 100 μW/cm$^2$ to approximately 10 W/cm$^2$) at the target tissue site, and time periods of application of the light energy at a few seconds to minutes to achieve an efficacious energy density at the target tissue site being treated. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.

Element to Inhibit Temperature Increases at the Scalp

Figure 1:
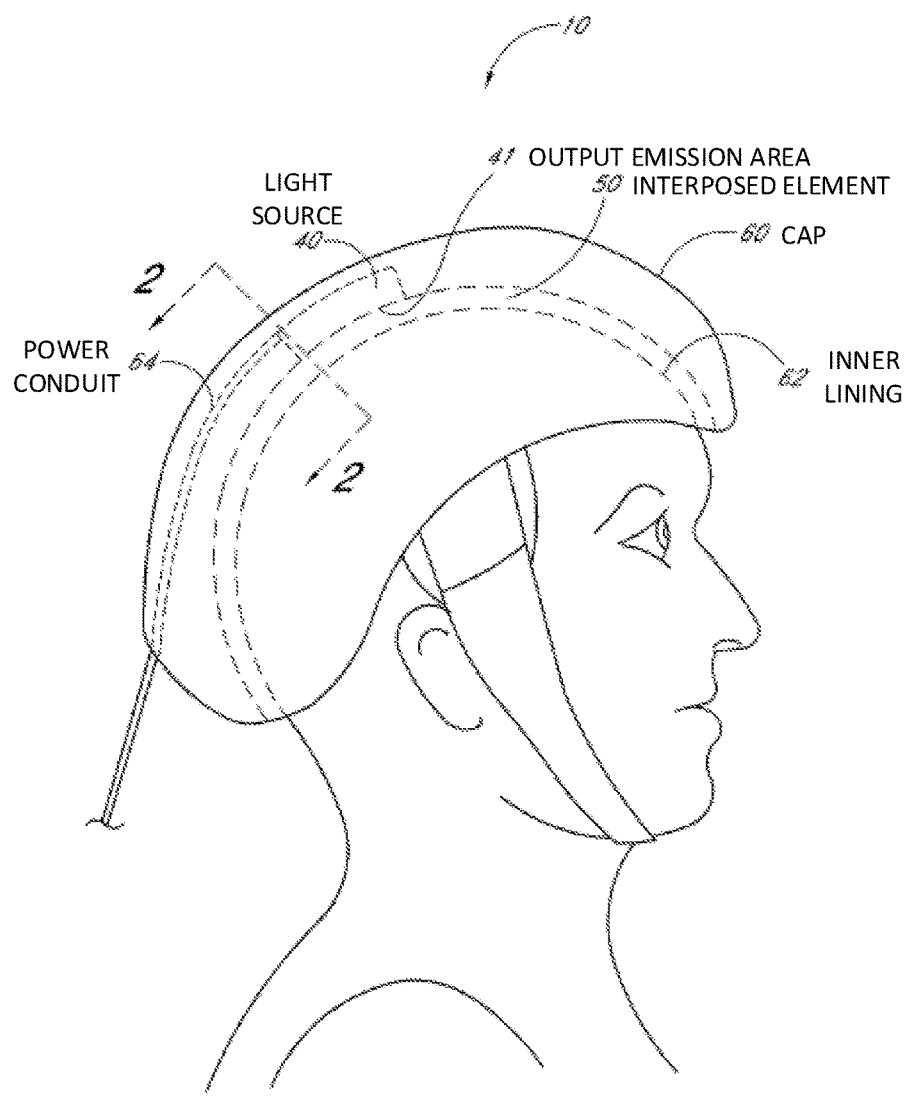
FIG. 1 schematically illustrates a therapy apparatus comprising a cap which fits securely over the patient's head.
Figure 2:
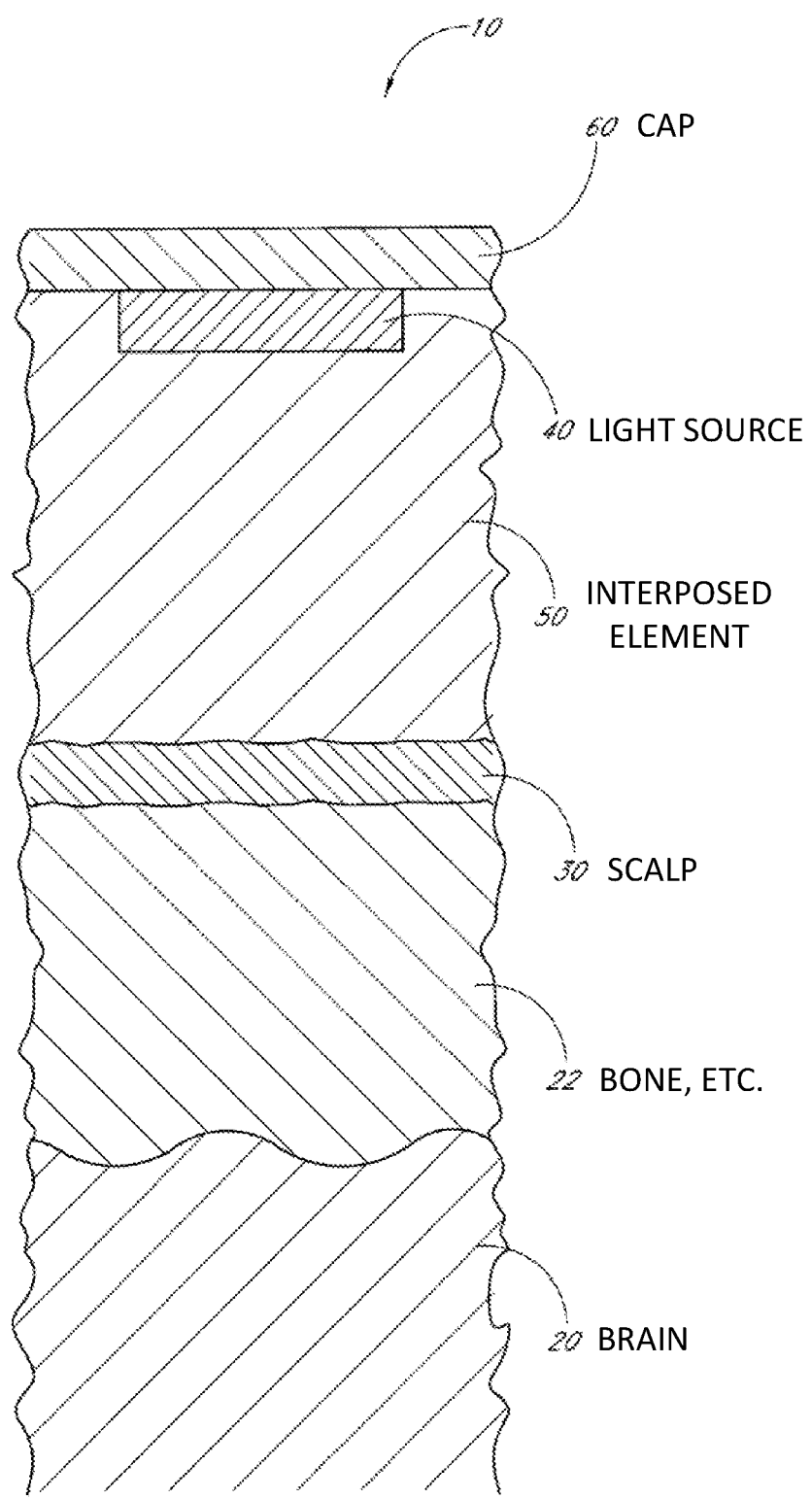
FIG. 2 schematically illustrates a fragmentary cross-sectional view taken along the lines 2-2 of FIG. 1, showing one embodiment of a portion of a therapy apparatus comprising an element and its relationship to the scalp and brain.

FIGS. 1 and 2 schematically illustrate an embodiment of a therapy apparatus 10 for treating a patient's brain 20. The therapy apparatus 10 comprises a light source 40 having an output emission area 41 positioned to irradiate a portion of the brain 20 with an efficacious power density and wavelength of light. The therapy apparatus 10 further comprises an element 50 interposed between the light source 40 and the patient's scalp 30. The element 50 is adapted to inhibit temperature increases at the scalp 30 caused by the light.

As used herein, the term "element" is used in its broadest sense, including, but not limited to, as a reference to a constituent or distinct part of a composite device. In certain embodiments, the element 50 is adapted to contact at least a portion of the patient's scalp 30, as schematically illustrated in FIGS. 1-4. In certain such embodiments, the element 50 is in thermal communication with and covers at least a portion of the scalp 30. In other embodiments, the element 50 is spaced away from the scalp 30 and does not contact the scalp 30.

In certain embodiments, the light passes through the element 50 prior to reaching the scalp 30 such that the element 50 is in the optical path of light propagating from the light source 40, through the scalp 30, through the bones, tissues, and fluids of the head (schematically illustrated in FIG. 1 by the region 22), to the brain 20. In certain embodiments, the light passes through a transmissive medium of the element 50, while in other embodiments, the light passes through an aperture of the element 50. As described more fully below, the element 50 may be utilized with various embodiments of the therapy apparatus 10.

In certain embodiments, the light source 40 is disposed on the interior surface of a cap 60 which fits securely over the patient's head. The cap 60 provides structural integrity for the therapy apparatus 10 and holds the light source 40 and element 50 in place. Exemplary materials for the cap 60 include, but are not limited to, metal, plastic, or other materials with appropriate structural integrity. The cap 60 may include an inner lining 62 comprising a stretchable fabric or mesh material, such as Lycra or nylon. In certain embodiments, the light source 40 is adapted to be removably attached to the cap 60 in a plurality of positions so that the output emission area 41 of the light source 40 can be advantageously placed in a selected position for treatment of a stroke or CVA in any portion of the brain 20. In other embodiments, the light source 40 can be an integral portion of the cap 60.

The light source 40 illustrated by FIGS. 1 and 2 comprises at least one power conduit 64 coupled to a power source (not shown). In some embodiments, the power conduit 64 comprises an electrical conduit which is adapted to transmit electrical signals and power to an emitter (e.g., laser diode or light-emitting diode). In certain embodiments, the power conduit 64 comprises an optical conduit (e.g., optical waveguide) which transmits optical signals and power to the output emission area 41 of the light source 40. In certain such embodiments, the light source 40 comprises optical elements (e.g., lenses, diffusers, and/or waveguides) which transmit at least a portion of the optical power received via the optical conduit 64. In still other embodiments, the therapy apparatus 10 contains a power source (e.g., a battery) and the power conduit 64 is substantially internal to the therapy apparatus 10.

In certain embodiments, the patient's scalp 30 comprises hair and skin which cover the patient's skull. In other embodiments, at least a portion of the hair is removed prior to the phototherapy treatment, so that the therapy apparatus 10 substantially contacts the skin of the scalp 30.

In certain embodiments, the element 50 is adapted to contact the patient's scalp 30, thereby providing an interface between the therapy apparatus 10 and the patient's scalp 30. In certain such embodiments, the element 50 is coupled to the light source 40 and in other such embodiments, the element is also adapted to conform to the scalp 30, as schematically illustrated in FIG. 1. In this way, the element 50 positions the output emission area 41 of the light source 40 relative to the scalp 30. In certain such embodiments, the element 50 is mechanically adjustable so as to adjust the position of the light source 40 relative to the scalp 30. By fitting to the scalp 30 and holding the light source 40 in place, the element 50 inhibits temperature increases at the scalp 30 that would otherwise result from misplacement of the light source 40 relative to the scalp 30. In addition, in certain embodiments, the element 50 is mechanically adjustable so as to fit the therapy apparatus 10 to the patient's scalp 30.

In certain embodiments, the element 50 provides a reusable interface between the therapy apparatus 10 and the patient's scalp 30. In such embodiments, the element 50 can be cleaned or sterilized between uses of the therapy apparatus, particularly between uses by different patients. In other embodiments, the element 50 provides a disposable and replaceable interface between the therapy apparatus 10 and the patient's scalp 30. By using pre-sterilized and pre-packaged replaceable interfaces, certain embodiments can advantageously provide sterilized interfaces without undergoing cleaning or sterilization processing immediately before use.

In certain embodiments, the element 50 comprises a container (e.g., a cavity or bag) containing a material (e.g., gel or liquid). The container can be flexible and adapted to conform to the contours of the scalp 30. Other exemplary materials contained in the container of the element 50 include, but are not limited to, thermal exchange materials such as glycerol and water. The element 50 of certain embodiments substantially covers the entire scalp 30 of the patient, as schematically illustrated in FIG. 2. In other embodiments, the element 50 only covers a localized portion of the scalp 30 in proximity to the irradiated portion of the scalp 30.

In certain embodiments, at least a portion of the element 50 is within an optical path of the light from the light source 40 to the scalp 30. In such embodiments, the element 50 is substantially optically transmissive at a wavelength of the light emitted by the output emission area 41 of the light source 40 and is adapted to reduce back reflections of the light. By reducing back reflections, the element 50 increases the amount of light transmitted to the brain 20 and reduces the need to use a higher power light source 40 which may otherwise create temperature increases at the scalp 30. In certain such embodiments, the element 50 comprises one or more optical coatings, films, layers, membranes, etc. in the optical path of the transmitted light which are adapted to reduce back reflections.

In certain such embodiments, the element 50 reduces back reflections by fitting to the scalp 30 so as to substantially reduce air gaps between the scalp 30 and the element 50 in the optical path of the light. The refractive-index mismatches between such an air gap and the element 50 and/or the scalp 30 would otherwise result in at least a portion of the light propagating from the light source 40 to the brain 20 to be reflected back towards the light source 40.

In addition, certain embodiments of the element 50 comprise a material having, at a wavelength of light emitted by the light source 40, a refractive index which substantially matches the refractive index of the scalp 30 (e.g., about 1.3), thereby reducing any index-mismatch-generated back reflections between the element 50 and the scalp 30. Examples of materials with refractive indices compatible with embodiments described herein include, but are not limited to, glycerol, water, and silica gels. Exemplary index-matching gels include, but are not limited to, those available from Nye Lubricants, Inc. of Fairhaven, Mass.

In certain embodiments, the element 50 is adapted to cool the scalp 30 by removing heat from the scalp 30 so as to inhibit temperature increases at the scalp 30. In certain such embodiments, the element 50 comprises a reservoir (e.g., a chamber or a conduit) adapted to contain a coolant. The coolant flows through the reservoir near the scalp 30. The scalp 30 heats the coolant, which flows away from the scalp 30, thereby removing heat from the scalp 30 by active cooling. The coolant in certain embodiments circulates between the element 50 and a heat transfer device, such as a chiller, whereby the coolant is heated by the scalp 30 and is cooled by the heat transfer device. Exemplary materials for the coolant include, but are not limited to, water or air.

Figure 3:
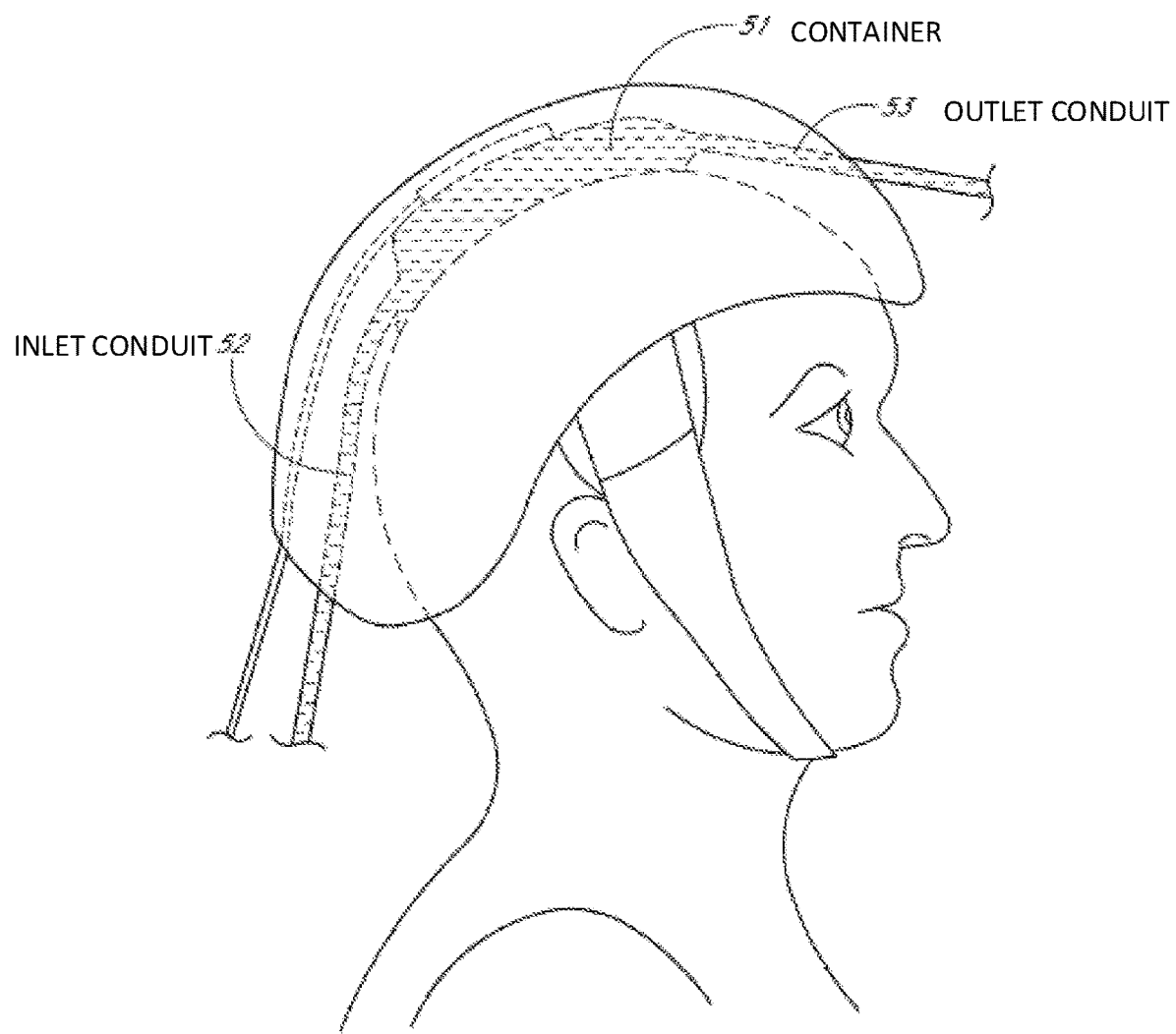
FIG. 3 schematically illustrates an embodiment with an element comprising a container coupled to an inlet conduit and an outlet conduit for the transport of a flowing material through the element.

In certain embodiments, the element 50 comprises a container 51 (e.g., a flexible bag) coupled to an inlet conduit 52 and an outlet conduit 53, as schematically illustrated in FIG. 3. A flowing material (e.g., water, air, or glycerol) can flow into the container 51 from the inlet conduit 52, absorb heat from the scalp 30, and flow out of the container 51 through the outlet conduit 53. Certain such embodiments can provide a mechanical fit of the container 51 to the scalp 30 and sufficient thermal coupling to prevent excessive heating of the scalp 30 by the light. In certain embodiments, the container 51 can be disposable and replacement containers 51 can be used for subsequent patients.

In still other embodiments, the element 50 comprises a container (e.g., a flexible bag) containing a material which does not flow out of the container but is thermally coupled to the scalp 30 so as to remove heat from the scalp 30 by passive cooling. Exemplary materials include, but are not limited to, water, glycerol, and gel. In certain such embodiments, the non-flowing material can be pre-cooled (e.g., by placement in a refrigerator) prior to the phototherapy treatment to facilitate cooling of the scalp 30.

In certain embodiments, the element 50 is adapted to apply pressure to at least a portion of the scalp 30. By applying sufficient pressure, the element 50 can blanch the portion of the scalp 30 by forcing at least some blood out the optical path of the light energy. The blood removal resulting from the pressure applied by the element 50 to the scalp 30 decreases the corresponding absorption of the light energy by blood in the scalp 30. As a result, temperature increases due to absorption of the light energy by blood at the scalp 30 are reduced. As a further result, the fraction of the light energy transmitted to the subdermal target tissue of the brain 20 is increased.

Figure 4A:
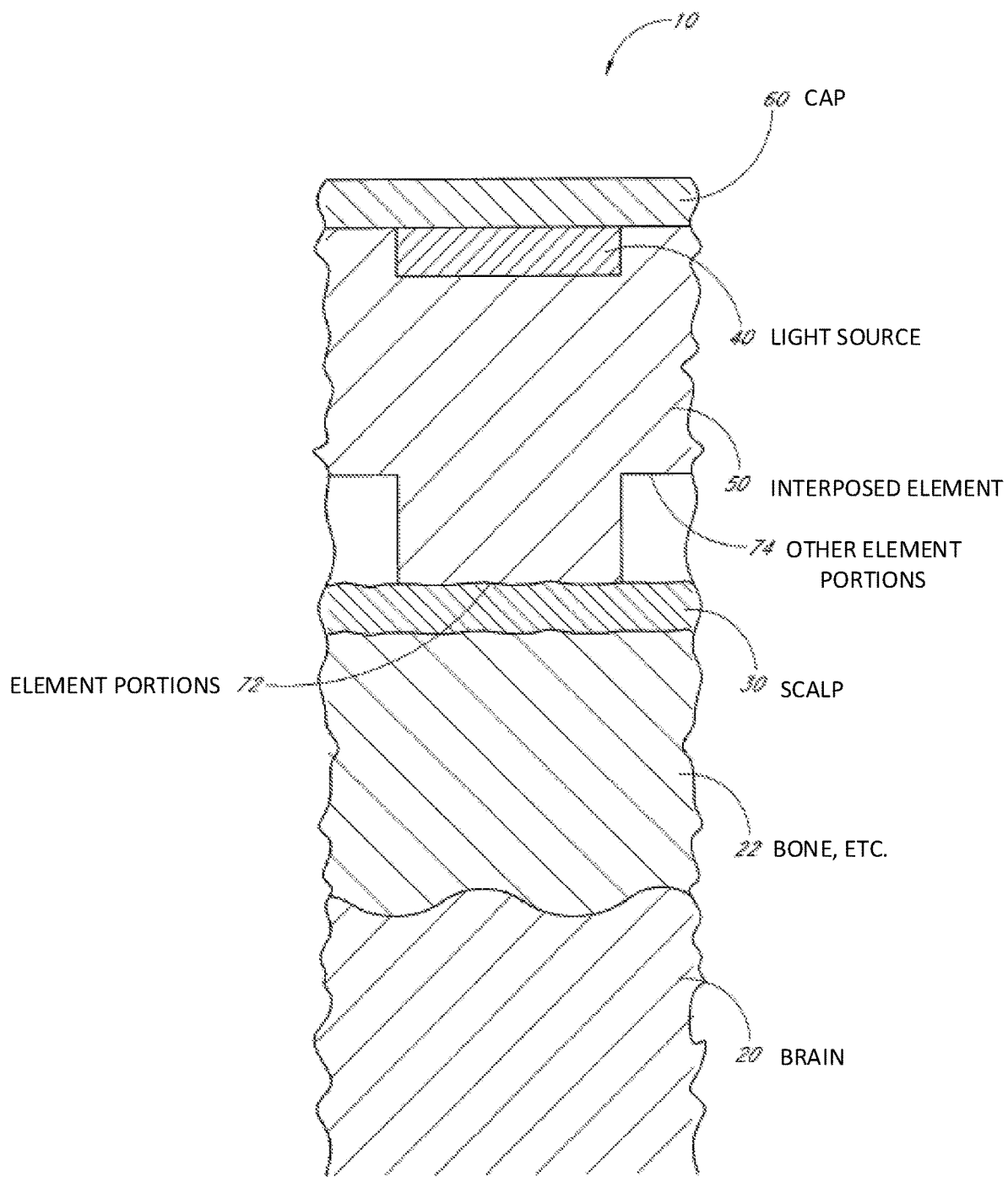
FIG. 4A schematically illustrates a fragmentary cross-sectional view taken along the lines 2-2 of FIG. 1, showing another embodiment of a portion of a therapy apparatus comprising an element with a portion contacting the scalp and a portion spaced away from the scalp.
Figure 4B:
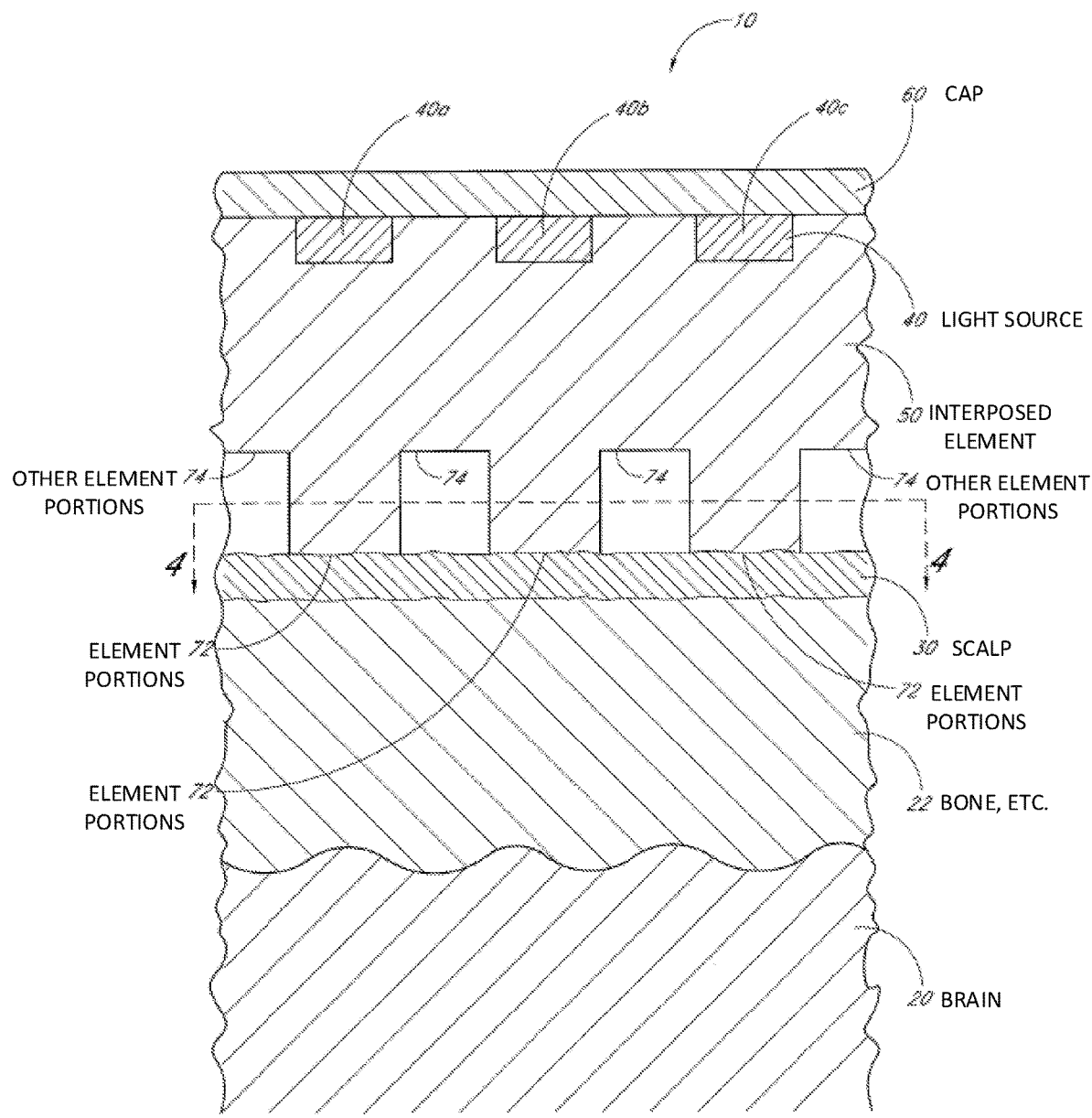
FIG. 4B schematically illustrates a fragmentary cross-sectional view taken along the lines 2-2 of FIG. 1, showing an embodiment of a portion of a therapy apparatus comprising a plurality of light sources and an element with portions contacting the scalp and portions spaced away from the scalp.

FIGS. 4A and 4B schematically illustrate embodiments of the element 50 adapted to facilitate the blanching of the scalp 30. In the cross-sectional view of a portion of the therapy apparatus 10 schematically illustrated in FIG. 4A, certain element portions 72 contact the patient's scalp 30 and other element portions 74 are spaced away from the scalp 30. The element portions 72 contacting the scalp 30 provide an optical path for light to propagate from the light source 40 to the scalp 30. The element portions 72 contacting the scalp 30 also apply pressure to the scalp 30, thereby forcing blood out from beneath the element portion 72. FIG. 4B schematically illustrates a similar view of an embodiment in which the light source 40 comprises a plurality of light sources 40a, 40b, 40c.

Figure 5A:
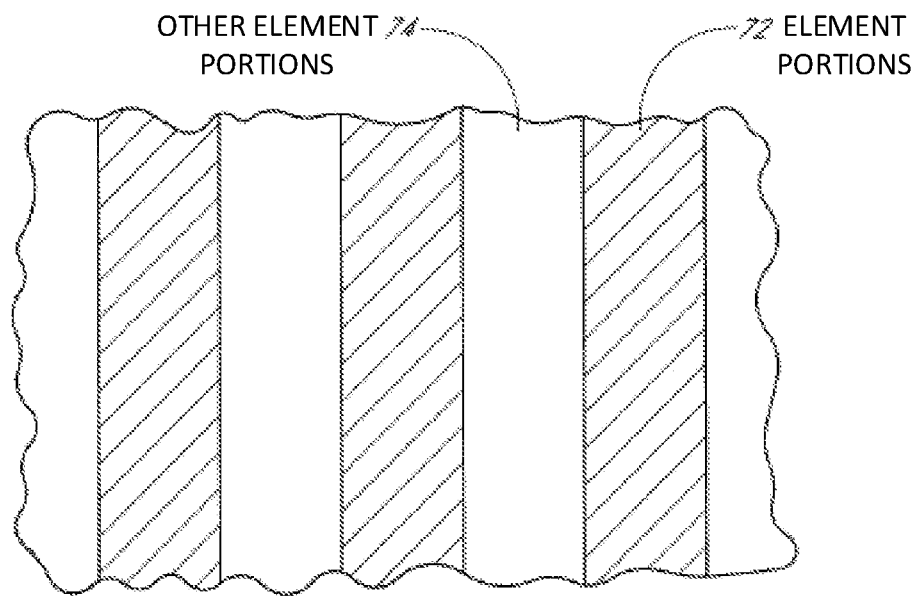
FIGS. 5A and 5B schematically illustrate cross-sectional views of two embodiments of the element in accordance with FIG. 4B taken along the line 4-4.
Figure 5B:
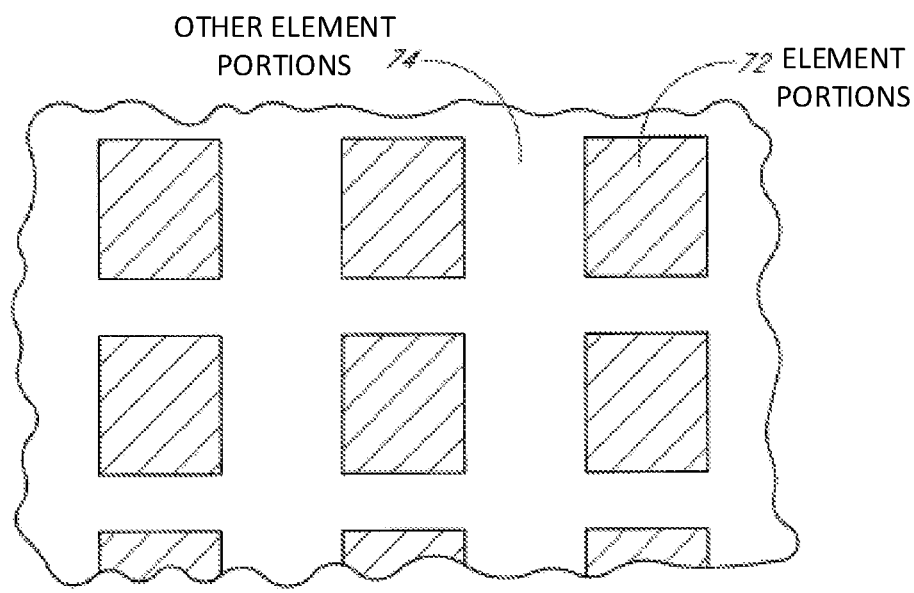

FIG. 5A schematically illustrates one embodiment of the cross-section along the line 4-4 of FIG. 4B. The element portions 72 contacting the scalp 30 comprise ridges extending along one direction, and the element portions 74 spaced away from the scalp 30 comprise troughs extending along the same direction. In certain embodiments, the ridges are substantially parallel to one another and the troughs are substantially parallel to one another. FIG. 5B schematically illustrates another embodiment of the cross-section along the line 4-4 of FIG. 4B. The element portions 72 contacting the scalp 30 comprise a plurality of projections in the form of a grid or array. More specifically, the portions 72 are rectangular and are separated by element portions 74 spaced away from the scalp 30, which form troughs extending in two substantially perpendicular directions. The portions 72 of the element 50 contacting the scalp 30 can be a substantial fraction of the total area of the element 50 or of the scalp 30.

Figure 6A:
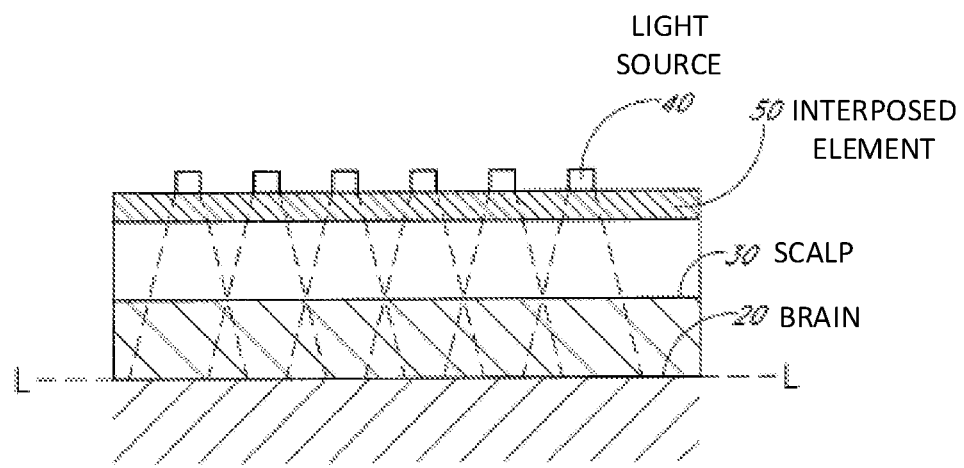
FIGS. 6A-6C schematically illustrate an embodiment in which the light sources are spaced away from the scalp.
Figure 6B:
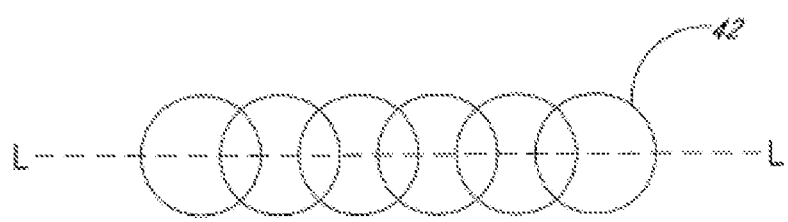
Figure 6C:
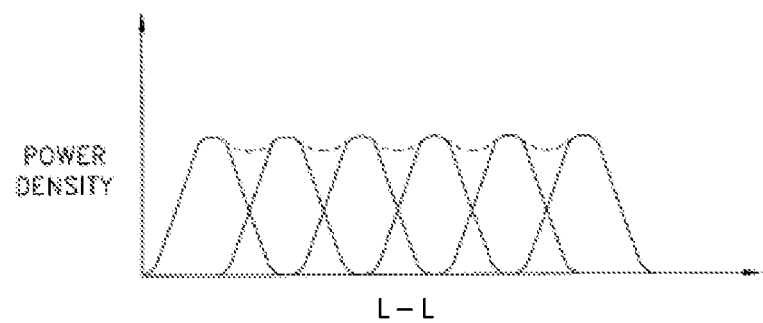

FIGS. 6A-6C schematically illustrate an embodiment in which the light sources 40 are spaced away from the scalp 30. In certain such embodiments, the light emitted by the light sources 40 propagates from the light sources 40 through the scalp 30 to the brain 20 and disperses in a direction generally parallel to the scalp 30, as shown in FIG. 6A. The light sources 40 are preferably spaced sufficiently far apart from one another such that the light emitted from each light source 40 overlaps with the light emitted from the neighboring light sources 40 at the brain 20. FIG. 6B schematically illustrates this overlap as the overlap of circular spots 42 at a reference depth at or below the surface of the brain 20. FIG. 6C schematically illustrates this overlap as a graph of the power density at the reference depth of the brain 20 along the line L-L of FIGS. 6A and 6B. Summing the power densities from the neighboring light sources 40 (shown as a dashed line in FIG. 6C) serves to provide a more uniform light distribution at the tissue to be treated. In such embodiments, the summed power density is preferably less than a damage threshold of the brain 20 and above an efficacy threshold.

Figure 7A:
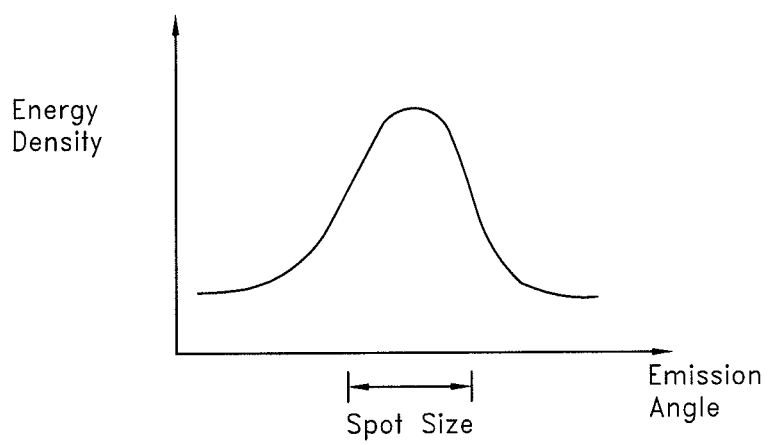
FIGS. 7A and 7B schematically illustrate the diffusive effect on the light by the element.
Figure 7B:
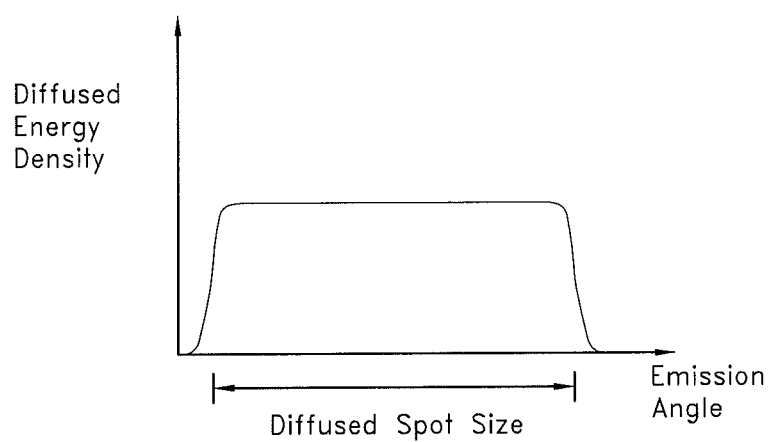

In certain embodiments, the element 50 is adapted to diffuse the light prior to reaching the scalp 30. FIGS. 7A and 7B schematically illustrate the diffusive effect on the light by the element 50. An exemplary energy density profile of the light emitted by a light source 40, as illustrated by FIG. 7A, is peaked at a particular emission angle. After being diffused by the element 50, as illustrated by FIG. 7B, the energy density profile of the light does not have a substantial peak at any particular emission angle, but is substantially evenly distributed among a range of emission angles. By diffusing the light emitted by the light source 40, the element 50 distributes the light energy substantially evenly over the area to be illuminated, thereby inhibiting "hot spots" which would otherwise create temperature increases at the scalp 30. In addition, by diffusing the light prior to its reaching the scalp 30, the element 50 can effectively increase the spot size of the light impinging the scalp 30, thereby advantageously lowering the power density at the scalp 30, as described more fully below. In addition, in embodiments with multiple light sources 40, the element 50 can diffuse the light to alter the total light output distribution to reduce inhomogeneities.

In certain embodiments, the element 50 provides sufficient diffusion of the light such that the power density of the light is less than a maximum tolerable level of the scalp 30 and brain 20. In certain other embodiments, the element 50 provides sufficient diffusion of the light such that the power density of the light equals a therapeutic value at the target tissue. The element 50 can comprise exemplary diffusers including, but are not limited to, holographic diffusers such as those available from Physical Optics Corp. of Torrance, Calif. and Display Optics P/N SN1333 from Reflexite Corp. of Avon, Conn.

Power Density

Phototherapy for the treatment of stroke is based in part on the discovery that power density (i.e., power per unit area or number of photons per unit area per unit time) and energy density (i.e., energy per unit area or number of photons per unit area) of the light energy applied to tissue appear to be significant factors in determining the relative efficacy of low level phototherapy. This discovery is particularly applicable with respect to treating and saving surviving but endangered neurons in a zone of danger surrounding the primary infarct after a stroke or cerebrovascular accident (CVA). Preferred methods described herein are based at least in part on the finding that, given a selected wavelength of light energy, it is the power density and/or the energy density of the light delivered to tissue (as opposed to the total power or total energy delivered to the tissue) that appears to be important factors in determining the relative efficacy of phototherapy.

Without being bound by theory, it is believed that light energy delivered within a certain range of power densities and energy densities provides the desired biostimulative effect on the intracellular environment, such that proper function is returned to previously nonfunctioning or poorly functioning mitochondria in at-risk neurons. The biostimulative effect may include interactions with chromophores within the target tissue, which facilitate production of ATP thereby feeding energy to injured cells which have experienced decreased blood flow due to the stroke. Because strokes correspond to blockages or other interruptions of blood flow to portions of the brain, it is thought that any effects of increasing blood flow by phototherapy are of less importance in the efficacy of phototherapy for stroke victims. Further information regarding the role of power density and exposure time is described by Hans H. F. I. van Breugel and P. R. Dop Bär in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein.

Figure 8B:
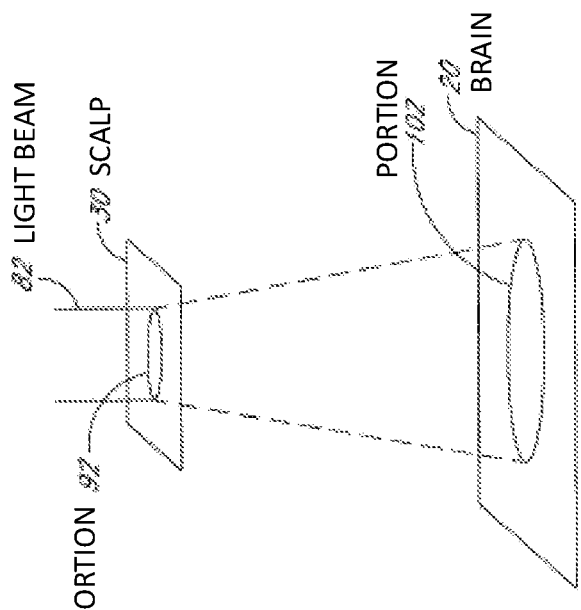
FIGS. 8A and 8B schematically illustrate two light beams having different cross-sections impinging a patient's scalp and propagating through the patient's head to irradiate a portion of the patient's brain tissue.
Figure 8A:
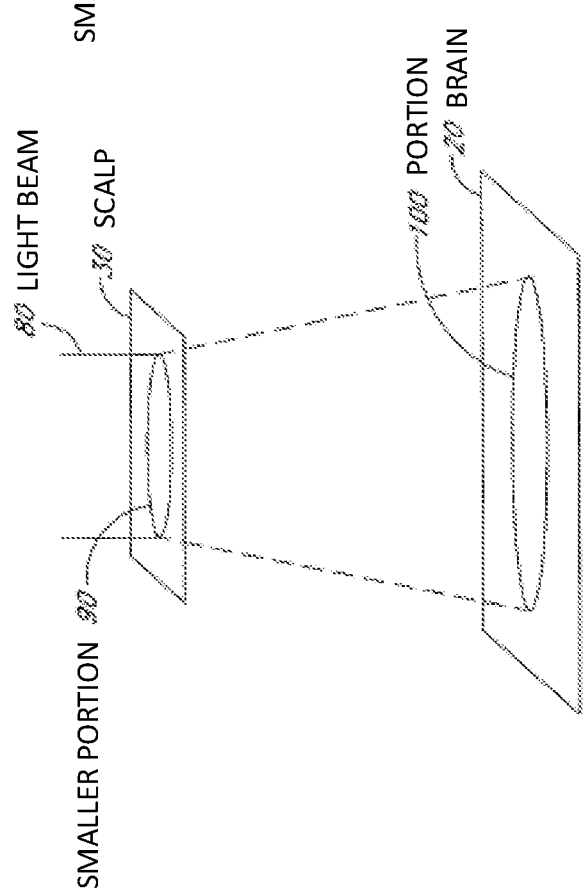

The significance of the power density used in phototherapy has ramifications with regard to the devices and methods used in phototherapy of brain tissue, as schematically illustrated by FIGS. 8A and 8B, which show the effects of scattering by intervening tissue. Further information regarding the scattering of light by tissue is provided by V. Tuchin in "Tissue Optics: Light Scattering Methods and Instruments for Medical Diagnosis," SPIE Press (2000), Bellingham, Wash., pp. 3-11, which is incorporated in its entirety by reference herein.

FIG. 8A schematically illustrates a light beam 80 impinging a portion 90 of a patient's scalp 30 and propagating through the patient's head to irradiate a portion 100 of the patient's brain tissue 20. In the exemplary embodiment of FIG. 8A, the light beam 80 impinging the scalp 30 is collimated and has a circular cross-section with a radius of 2 cm and a cross-sectional area of approximately 12.5 $cm^2$. For comparison purposes, FIG. 8B schematically illustrates a light beam 82 having a significantly smaller cross-section impinging a smaller portion 92 of the scalp 30 to irradiate a portion 102 of the brain tissue 20. The light beam 82 impinging the scalp 30 in FIG. 8B is collimated and has a circular cross-section with a radius of 1 cm and a cross-sectional area of approximately 3.1 $cm^2$. The collimations, cross-sections, and radii of the light beams 80, 82 illustrated in FIGS. 8A and 8B are exemplary; other light beams with other parameters are also compatible with embodiments described herein. In particular, similar considerations apply to focused beams or diverging beams, as they are similarly scattered by the intervening tissue.

As shown in FIGS. 8A and 8B, the cross-sections of the light beams 80, 82 become larger while propagating through the head due to scattering from interactions with tissue of the head. Assuming that the angle of dispersion is 15 degrees and the irradiated brain tissue 20 is 2.5 cm below the scalp 30, the resulting area of the portion 100 of brain tissue 20 irradiated by the light beam 80 in FIG. 8A is approximately 22.4 $cm^2$. Similarly, the resulting area of the portion 102 of brain tissue 20 irradiated by the light beam 82 in FIG. 8B is approximately 8.8 $cm^2$.

Irradiating the portion 100 of the brain tissue 20 with a power density of 10 $mW/cm^2$ corresponds to a total power within the portion 100 of approximately 224 mW (10 $mW/cm^2 \times 22.4$ $cm^2$). Assuming only approximately 5% of the light beam 80 is transmitted between the scalp 30 and the brain tissue 20, the incident light beam 80 at the scalp 30 will have a total power of approximately 4480 mW (224 mW/0.05) and a power density of approximately 358 $mW/cm^2$ (4480 mW/12.5 $cm^2$). Similarly, irradiating the portion 102 of the brain tissue 20 with a power density of 10 $mW/cm^2$ corresponds to a total power within the portion 102 of approximately 88 mW (10 $mW/cm^2 \times 8.8$ $cm^2$), and with the same 5% transmittance, the incident light beam 82 at the scalp 30 will have a total power of approximately 1760 mW (88 mW/0.05) and a power density of approximately 568 $mW/cm^2$ (1760 mW/3.1 $cm^2$). These calculations are summarized in Table 1.

TABLE 1

|  | 2 cm Spot Size (FIG. 8A) | 1 cm Spot Size (FIG. 8B) |
|---|---|---|
| Scalp: | | |
| Area | 12.5 $cm^2$ | 3.1 $cm^2$ |
| Total power | 4480 mW | 1760 mW |
| Power density | 358 $mW/cm^2$ | 568 $mW/cm^2$ |
| Brain: | | |
| Area | 22.4 $cm^2$ | 8.8 $cm^2$ |
| Total power | 224 mW | 88 mW |
| Power density | 10 $mW/cm^2$ | 10 $mW/cm^2$ |

These exemplary calculations illustrate that to obtain a desired power density at the brain 20, higher total power at the scalp 30 can be used in conjunction with a larger spot size at the scalp 30. Thus, by increasing the spot size at the scalp 30, a desired power density at the brain 20 can be achieved with lower power densities at the scalp 30 which can reduce the possibility of overheating the scalp 30. In certain embodiments, the light can be directed through an aperture to define the illumination of the scalp 30 to a selected smaller area.

Light Source

In certain embodiments, a single light source 40 is used as a light generator to generate light, while in other embodiments, a plurality of light sources 40 are used as a light generator to generate light. The light source 40 preferably generates light in the visible to near-infrared wavelength range. In certain embodiments, the light source 40 comprises one or more laser diodes, which each provide coherent light. In embodiments in which the light from the light source 40 is coherent, the emitted light may produce "speckling" due to coherent interference of the light. This speckling comprises intensity spikes which are created by constructive interference and can occur in proximity to the target tissue being treated. For example, while the average power density may be approximately 10 $mW/cm^2$, the power density of one such intensity spike in proximity to the brain tissue to be treated may be approximately 300 $mW/cm^2$. In certain embodiments, this increased power density due to speckling can improve the efficacy of treatments using coherent light over those using incoherent light for illumination of deeper tissues.

In other embodiments, the light source 40 provides incoherent light. Exemplary light sources 40 of incoherent light include, but are not limited to, incandescent lamps or light-emitting diodes. A heat sink can be used with the light source 40 (for either coherent or incoherent sources) to remove heat from the light source 40 and to inhibit temperature increases at the scalp 30.

In certain embodiments, the light source 40 generates light which is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In other embodiments, the wavelength of the light is preferably between about 630 nanometers and about 1064 nanometers, more preferably between about 780 nanometers and about 840 nanometers, and most preferably includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) appears to be suitable for penetrating the skull, although other wavelengths are also suitable and may be used.

In other embodiments, the light source 40 generates light having a plurality of wavelengths. In certain such embodiments, each wavelength is selected so as to work with one or more chromophores within the target tissue. Without being bound by theory, it is believed that irradiation of chromophores increases the production of ATP in the target tissue, thereby producing beneficial effects. In certain embodiments, the light source 40 is adapted to generate light having a first wavelength concurrently with light having a second wavelength. In certain other embodiments, the light source 40 is adapted to generate light having a first wavelength sequentially with light having a second wavelength.

In certain embodiments, the light source 40 includes at least one continuously emitting GaAlAs laser diode having a wavelength of about 830 nanometers. In another embodiment, the light source 40 comprises a laser source having a wavelength of about 808 nanometers. In still other embodiments, the light source 40 includes at least one vertical cavity surface-emitting laser (VCSEL) diode. Other light sources 40 compatible with embodiments described herein include, but are not limited to, light-emitting diodes (LEDs) and filtered lamps.

The light source 40 is capable of emitting light energy at a power sufficient to achieve a predetermined power density at the subdermal target tissue (e.g., at a depth of approximately 2 centimeters from the dura). It is presently believed that phototherapy of tissue is most effective when irradiating the target tissue with power densities of light of at least about 0.01 mW/cm$^2$ and up to about 1 W/cm$^2$ at the level of the tissue. In various embodiments, the subsurface power density is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the subsurface power density at the target tissue is preferably about 0.01 mW/cm$^2$ to about 100 mW/cm$^2$, more preferably about 0.01 mW/cm$^2$ to about 50 mW/cm$^2$, and most preferably about 2 mW/cm$^2$ to about 20 mW/cm$^2$. It is believed that these subsurface power densities are especially effective at producing the desired biostimulative effects on the tissue being treated.

Taking into account the attenuation of energy as it propagates from the skin surface, through body tissue, bone, and fluids, to the subdermal target tissue, surface power densities preferably between about 10 mW/cm$^2$ to about 10 W/cm$^2$, or more preferably between about 100 mW/cm$^2$ to about 500 mW/cm$^2$, will typically be used to attain the selected power densities at the subdermal target tissue. To achieve such surface power densities, the light source 40 is preferably capable of emitting light energy having a total power output of at least about 25 mW to about 100 W. In various embodiments, the total power output is limited to be no more than about 30, 50, 75, 100, 150, 200, 250, 300, 400, or 500 mW, respectively. In certain embodiments, the light source 40 comprises a plurality of sources used in combination to provide the total power output. The actual power output of the light source 40 is preferably controllably variable. In this way, the power of the light energy emitted can be adjusted in accordance with a selected power density at the subdermal tissue being treated.

Certain embodiments utilize a light source 40 that includes only a single laser diode that is capable of providing about 25 mW to about 100 W of total power output at the skin surface. In certain such embodiments, the laser diode can be optically coupled to the scalp 30 via an optical fiber or can be configured to provide a sufficiently large spot size to avoid power densities which would burn or otherwise damage the scalp 30. In other embodiments, the light source 40 utilizes a plurality of sources (e.g., laser diodes) arranged in a grid or array that together are capable of providing at least about 25 mW to about 100 W of total power output at the skin surface. The light source 40 of other embodiments may also comprise sources having power capacities outside of these limits.

Figure 9A:
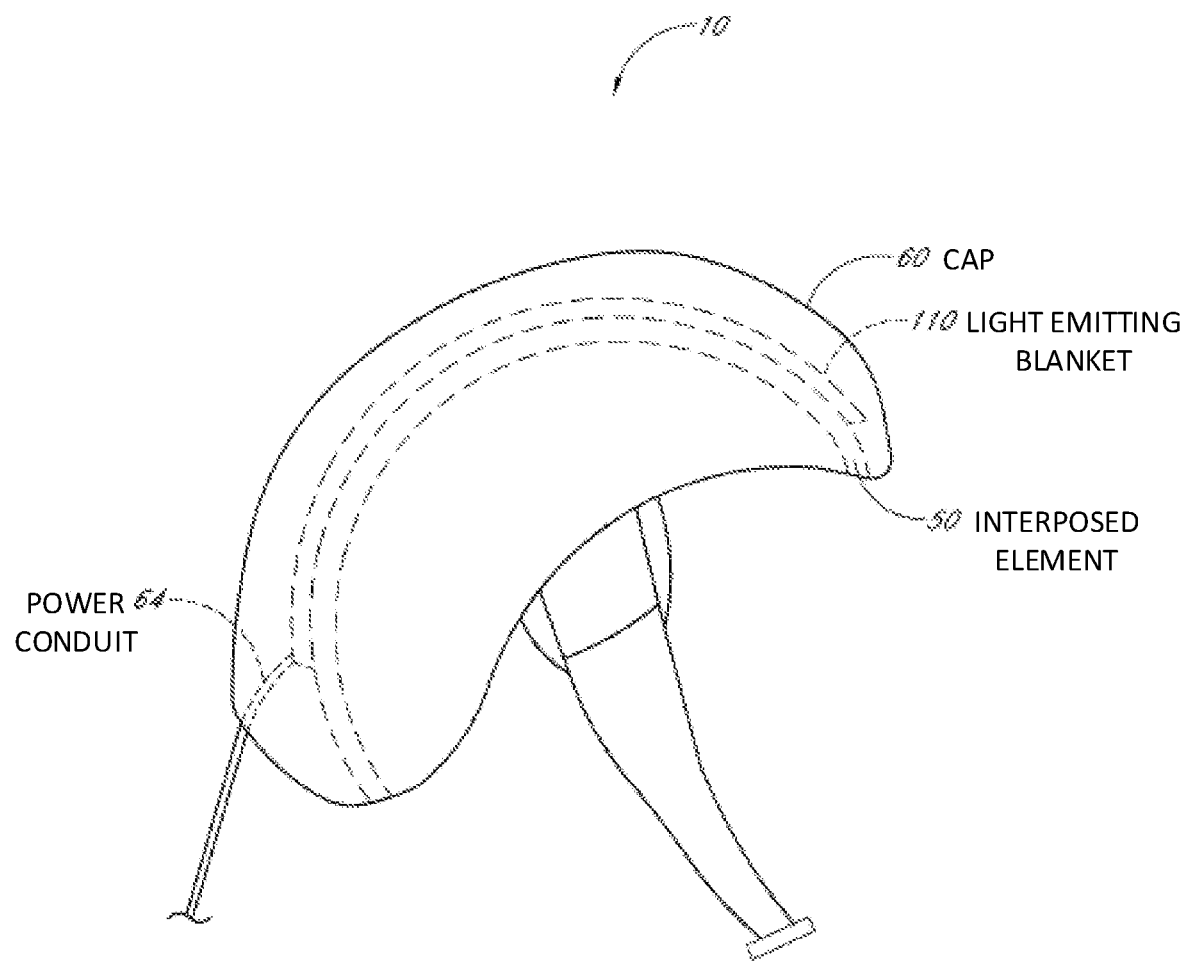
FIG. 9A schematically illustrates a therapy apparatus comprising a cap and a light source comprising a light blanket.
Figure 9B:
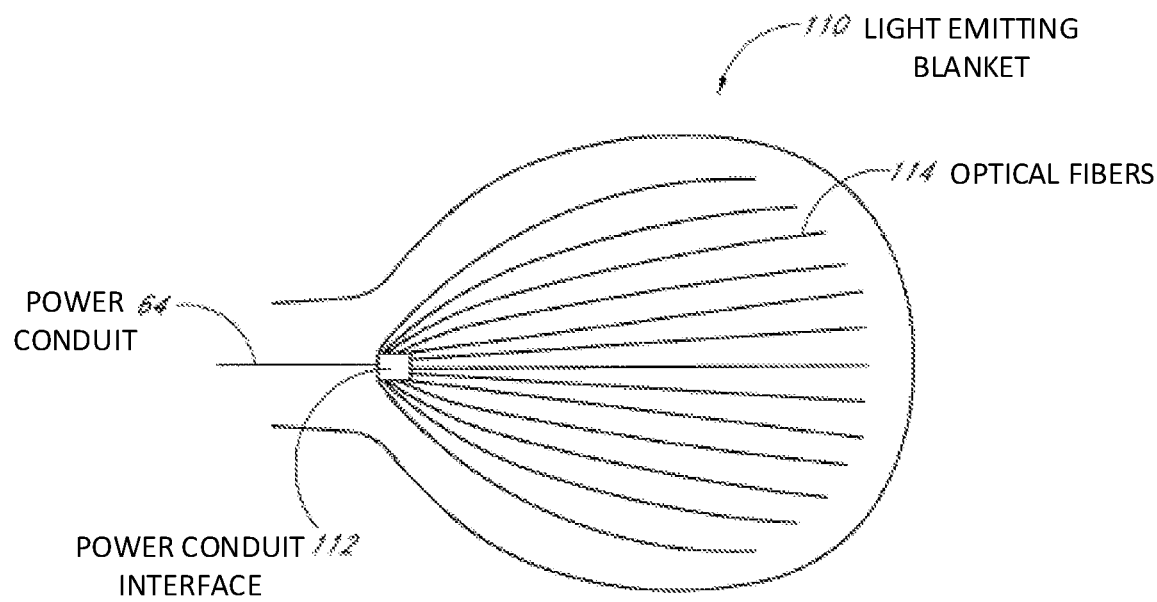
FIGS. 9B and 9C schematically illustrate two embodiments of the light blanket.
Figure 9C:
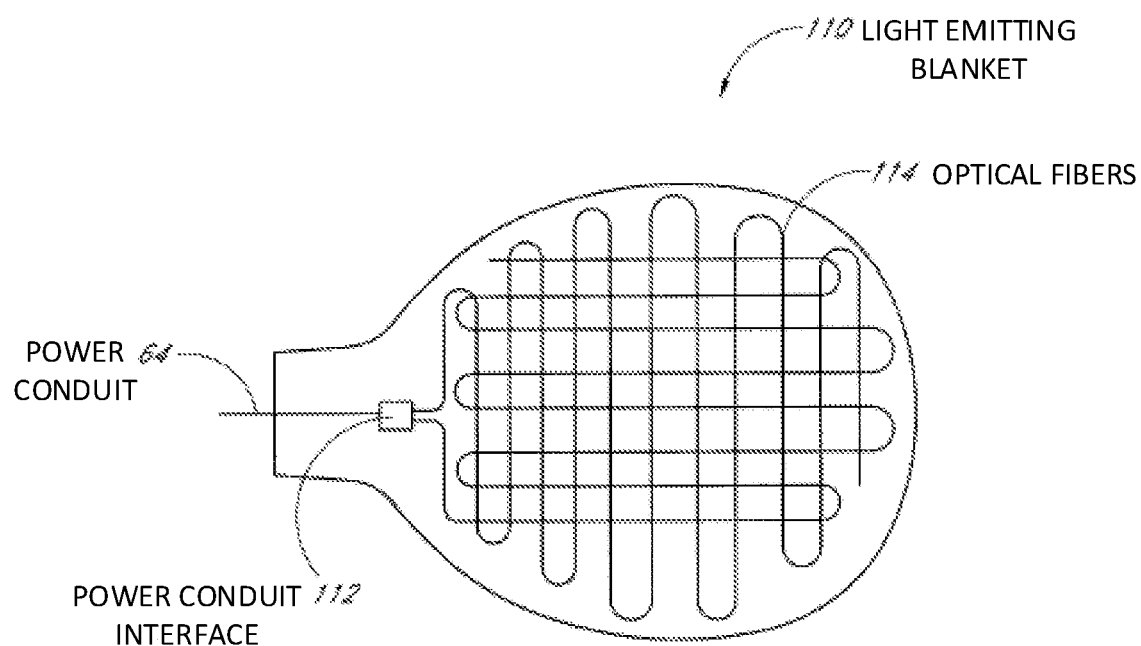

FIG. 9A schematically illustrates another embodiment of the therapy apparatus 10 which comprises the cap 60 and a light source comprising a light-emitting blanket 110. FIG. 9B schematically illustrates an embodiment of the blanket 110 comprising a flexible substrate 111 (e.g., flexible circuit board), a power conduit interface 112, and a sheet formed by optical fibers 114 positioned in a fan-like configuration. FIG. 9C schematically illustrates an embodiment of the blanket 110 comprising a flexible substrate 111, a power conduit interface 112, and a sheet formed by optical fibers 114 woven into a mesh. The blanket 110 is preferably positioned within the cap 60 so as to cover an area of the scalp 30 corresponding to a portion of the brain 20 to be treated.

In certain such embodiments, the power conduit interface 112 is adapted to be coupled to an optical fiber conduit 64 which provides optical power to the blanket 110. The optical power interface 112 of certain embodiments comprises a beam splitter or other optical device which distributes the incoming optical power among the various optical fibers 114. In other embodiments, the power conduit interface 112 is adapted to be coupled to an electrical conduit which provides electrical power to the blanket 110. In certain such embodiments, the power conduit interface 112 comprises one or more laser diodes, the output of which is distributed among the various optical fibers 114 of the blanket 110. In certain other embodiments, the blanket 110 comprises an electroluminescent sheet which responds to electrical signals from the power conduit interface 112 by emitting light. In such embodiments, the power conduit interface 112 comprises circuitry adapted to distribute the electrical signals to appropriate portions of the electroluminescent sheet.

The side of the blanket 110 nearer the scalp 30 is preferably provided with a light scattering surface, such as a roughened surface to increase the amount of light scattered out of the blanket 110 towards the scalp 30. The side of the blanket 110 further from the scalp 30 is preferably covered by a reflective coating so that light emitted away from the scalp 30 is reflected back towards the scalp 30. This configuration is similar to configurations used for the "back illumination" of liquid-crystal displays (LCDs). Other configurations of the blanket 110 are compatible with embodiments described herein.

In certain embodiments, the light source 40 generates light which cause eye damage if viewed by an individual. In such embodiments, the apparatus 50 can be configured to provide eye protection so as to avoid viewing of the light by individuals. For example, opaque materials can be appropriately placed to block the light from being viewed directly.

In addition, interlocks can be provided so that the light source 40 is not activated unless the apparatus 50 is in place, or other appropriate safety measures are taken.

Light Delivery Apparatuses

The phototherapy methods for the treatment of stroke described herein may be practiced and described using, for example, a low level laser therapy apparatus such as that shown and described in U.S. Pat. Nos. 6,214,035, 6,267,780, 6,273,905 and U.S. Pat. No. 6,290,714, which are all incorporated in their entirety by reference herein, as are the references incorporated by reference therein.

Figure 10:
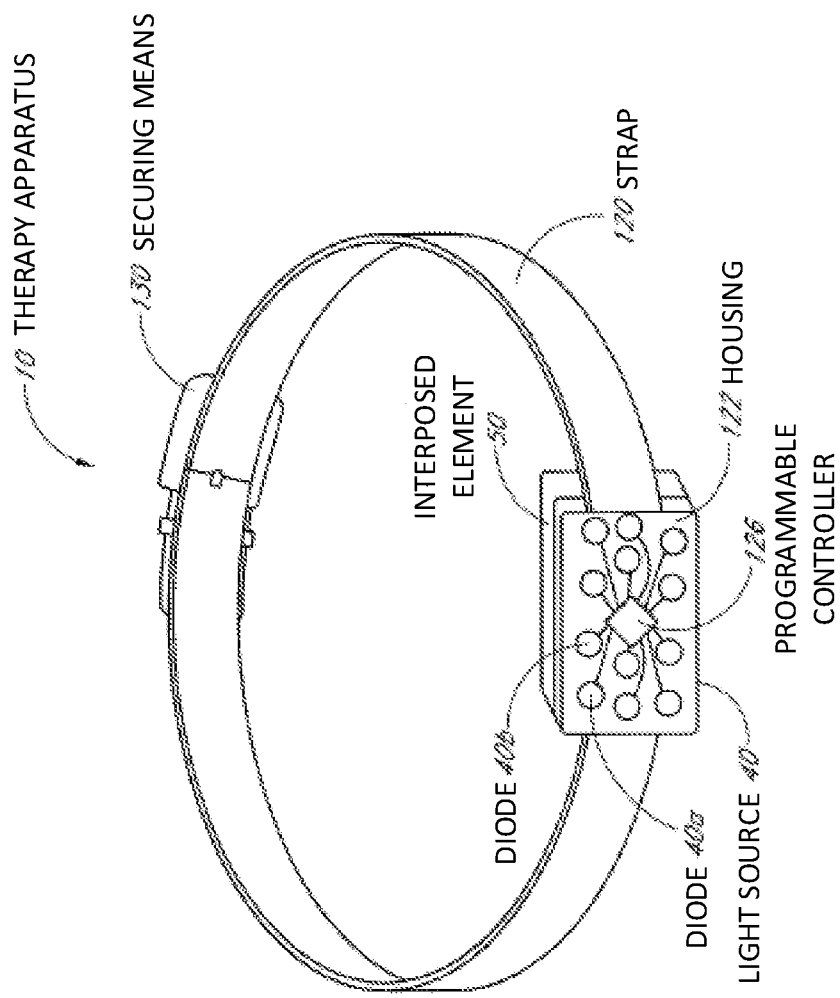
FIG. 10 schematically illustrates a therapy apparatus comprising a flexible strap and a housing.

Another suitable phototherapy apparatus in accordance with embodiments described here is illustrated in FIG. 10. The illustrated therapy apparatus 10 includes a light source 40, an element 50, and a flexible strap 120 adapted for securing the therapy apparatus 10 over an area of the patient's head. The light source 40 can be disposed on the strap 120 itself, or in a housing 122 coupled to the strap 120. The light source 40 preferably comprises a plurality of diodes 40a, 40b, etc. capable of emitting light energy having a wavelength in the visible to near-infrared wavelength range. The element 50 is adapted to be positioned between the light source 40 and the patient's scalp 30.

The therapy apparatus 10 further includes a power supply (not shown) operatively coupled to the light source 40, and a programmable controller 126 operatively coupled to the light source 40 and to the power supply. The programmable controller 126 is configured to control the light source 40 so as to deliver a predetermined power density to the brain tissue 20. In certain embodiments, as schematically illustrated in FIG. 10, the light source 40 comprises the programmable controller 126. In other embodiments the programmable controller 126 is a separate component of the therapy apparatus 10.

In certain embodiments, the strap 120 comprises a loop of elastomeric material sized appropriately to fit snugly onto the patient's scalp 30. In other embodiments, the strap 120 comprises an elastomeric material to which is secured any suitable securing means 130, such as mating Velcro strips, buckles, snaps, hooks, buttons, ties, or the like. The precise configuration of the strap 120 is subject only to the limitation that the strap 120 is capable of maintaining the light source 40 in a selected position so that light energy emitted by the light source 40 is directed towards the targeted brain tissue 20.

In the exemplary embodiment illustrated in FIG. 10, the housing 122 comprises a layer of flexible plastic or fabric that is secured to the strap 120. In other embodiments, the housing 122 comprises a plate or an enlarged portion of the strap 120. Various strap configurations and spatial distributions of the light sources 40 are compatible with embodiments described herein so that the therapy apparatus 10 can treat selected portions of brain tissue.

Figure 11:
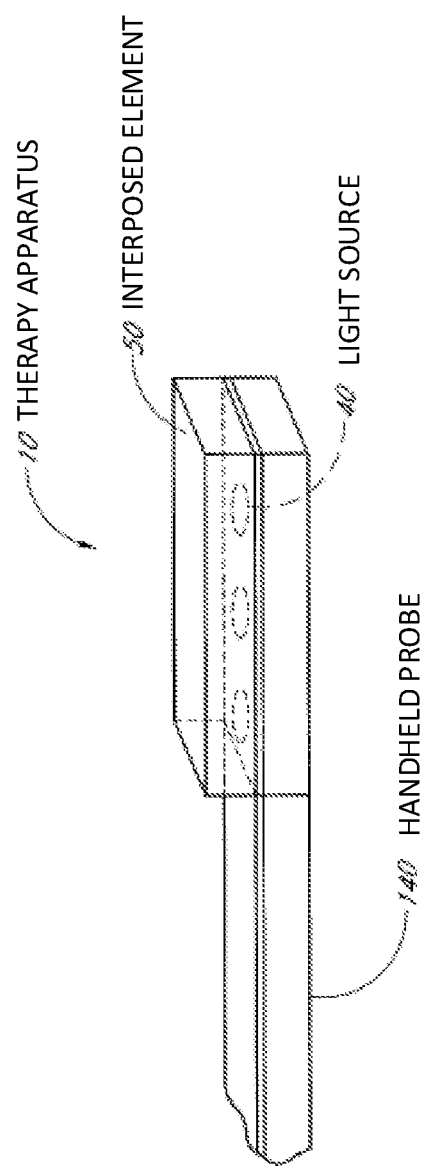
FIG. 11 schematically illustrates a therapy apparatus comprising a handheld probe.

In still other embodiments, the therapy apparatus 10 for delivering the light energy includes a handheld probe 140, as schematically illustrated in FIG. 11. The probe 140 includes a light source 40 and an element 50 as described herein.

Figure 12:
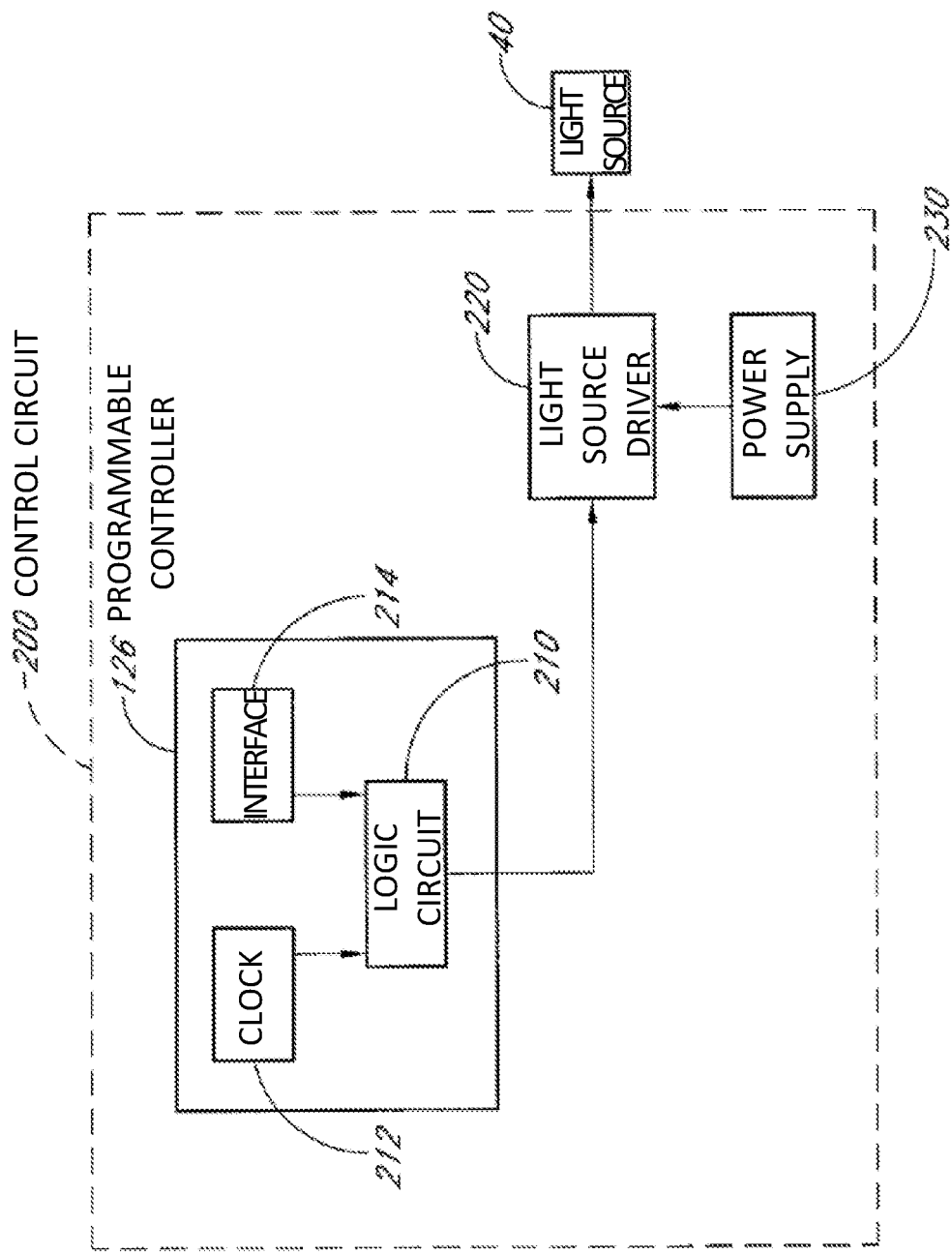
FIG. 12 is a block diagram of a control circuit comprising a programmable controller.

FIG. 12 is a block diagram of a control circuit 200 comprising a programmable controller 126 according to embodiments described herein. The control circuit 200 is configured to adjust the power of the light energy emitted by the light source 40 to generate a predetermined surface power density at the scalp 30 corresponding to a predetermined energy delivery profile, such as a predetermined subsurface power density, to the target area of the brain 20.

In certain embodiments, the programmable controller 126 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light sources 40 can be selectively turned on and off to reduce the thermal load on the scalp 30 and to deliver a selected power density to particular areas of the brain 20.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied power densities, target time intervals, and power density/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 40. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light sources 40. Other control circuits besides the control circuit 200 of FIG. 12 are compatible with embodiments described herein.

In certain embodiments, the logic circuit 110 is responsive to signals from a sensor monitoring at least one parameter of the treatment to control the applied light. For example, certain embodiments comprise a temperature sensor thermally coupled to the scalp 30 to provide information regarding the temperature of the scalp 30 to the logic circuit 210. In such embodiments, the logic circuit 210 is responsive to the information from the temperature sensor to transmit a control signal to the light source driver 220 so as to adjust the parameters of the applied light to maintain the scalp temperature below a predetermined level. Other embodiments include exemplary biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Figure 13:
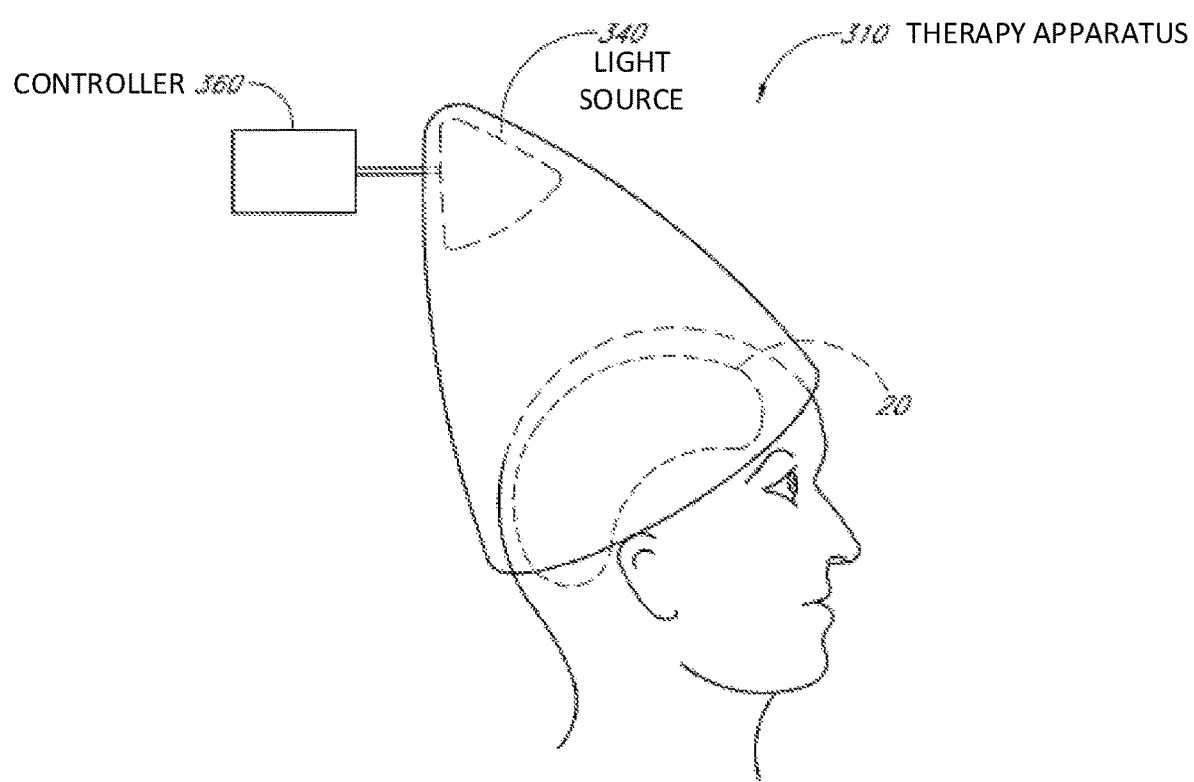
FIG. 13 schematically illustrates a therapy apparatus comprising a light source and a controller.

In certain embodiments, as schematically illustrated in FIG. 13, the therapy apparatus 310 comprises a light source 340 adapted to irradiate a portion of the patient's brain 20 with an efficacious power density and wavelength of light. The therapy apparatus 310 further comprises a controller 360 for energizing said light source 340, so as to selectively produce a plurality of different irradiation patterns on the patient's scalp 30. Each of the irradiation patterns is comprised of a least one illuminated area that is small compared to the patient's scalp 30, and at least one non-illuminated area.

Figure 14:
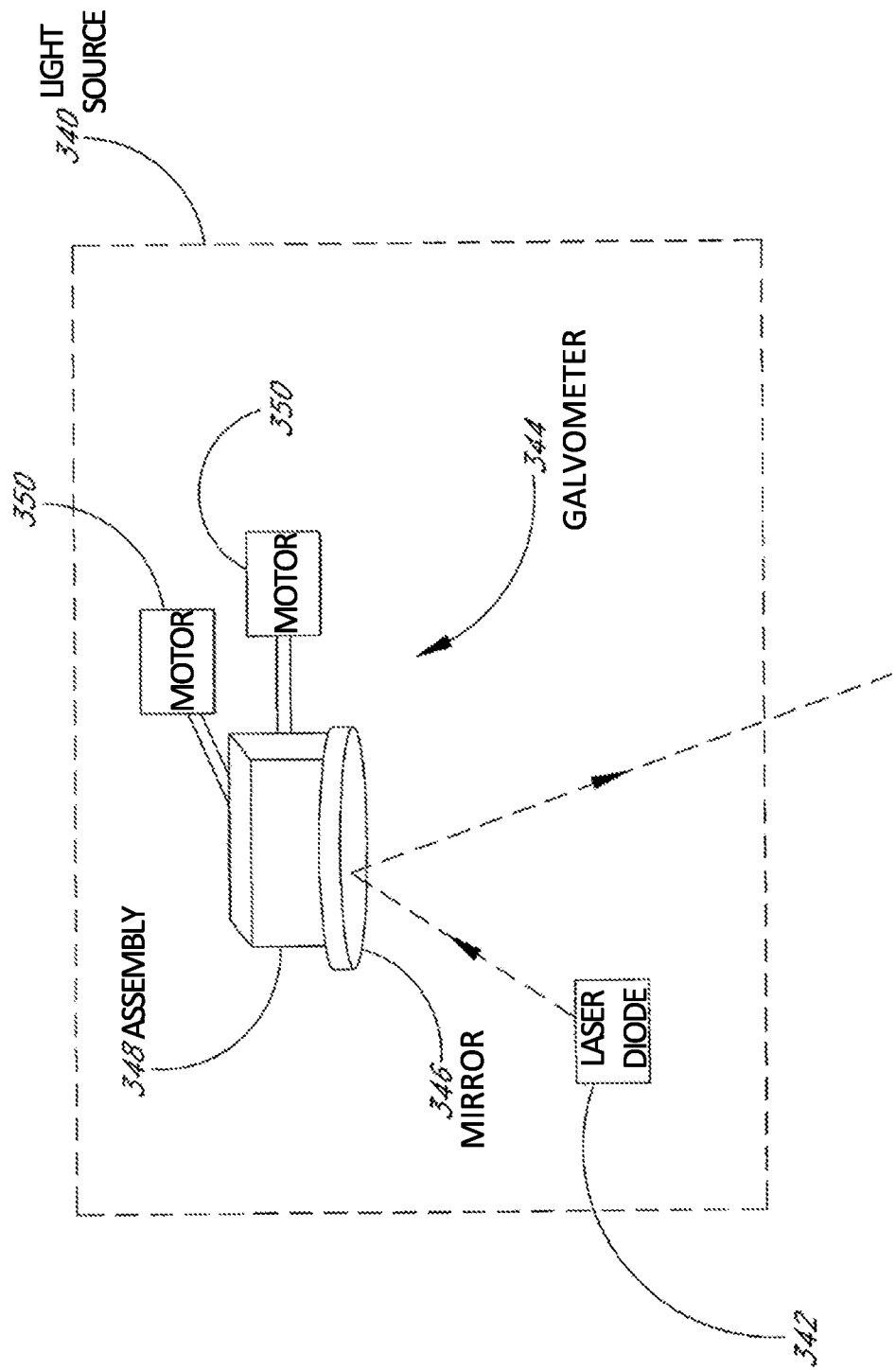
FIG. 14 schematically illustrates a light source comprising a laser diode and a galvometer with a mirror and a plurality of motors.

In certain embodiments, the light source 340 includes an apparatus for adjusting the emitted light to irradiate different portions of the scalp 30. In certain such embodiments, the apparatus physically moves the light source 40 relative to the scalp 30. In other embodiments, the apparatus does not move the light source 40, but redirects the emitted light to different portions of the scalp 30. In an exemplary embodiment, as schematically illustrated in FIG. 14, the light source 340 comprises a laser diode 342 and a galvometer 344, both of which are electrically coupled to the controller 360. The galvometer 344 comprises a mirror 346 mounted onto an assembly 348 which is adjustable by a plurality of motors 350. Light emitted by the laser diode 342 is directed toward the mirror 346 and is reflected to selected portions of the patient's scalp 30 by selectively moving the mirror 346 and selectively activating the laser diode 342. In certain embodiments, the therapy apparatus 310 comprises an element 50 adapted to inhibit temperature increases at the scalp 30 as described herein.

Figure 15A:
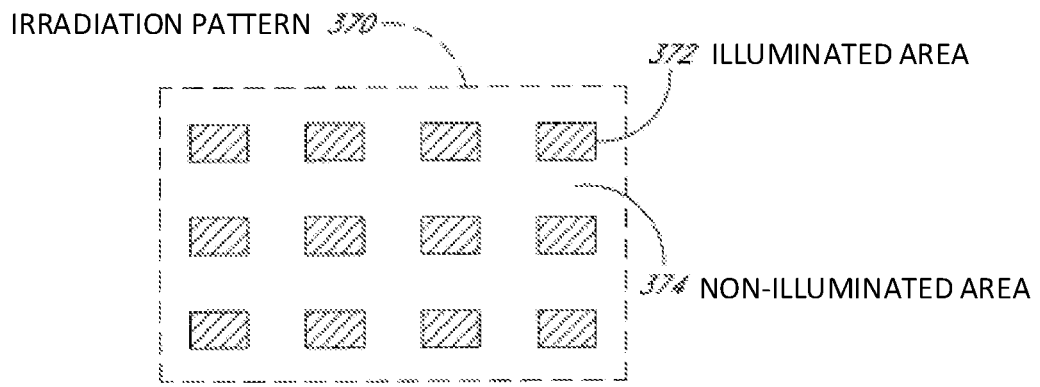
FIGS. 15A and 15B schematically illustrate two irradiation patterns that are spatially shifted relative to each other.

FIG. 15A schematically illustrates an irradiation pattern 370 in accordance with embodiments described herein. The irradiation pattern 370 comprises at least one illuminated area 372 and at least one non-illuminated area 374. In certain embodiments, the irradiation pattern 370 is generated by scanning the mirror 346 so that the light impinges the patient's scalp 30 in the illuminated area 372 but not in the non-illuminated area 374. Certain embodiments modify the illuminated area 372 and the non-illuminated area 374 as a function of time.

Figure 15B:
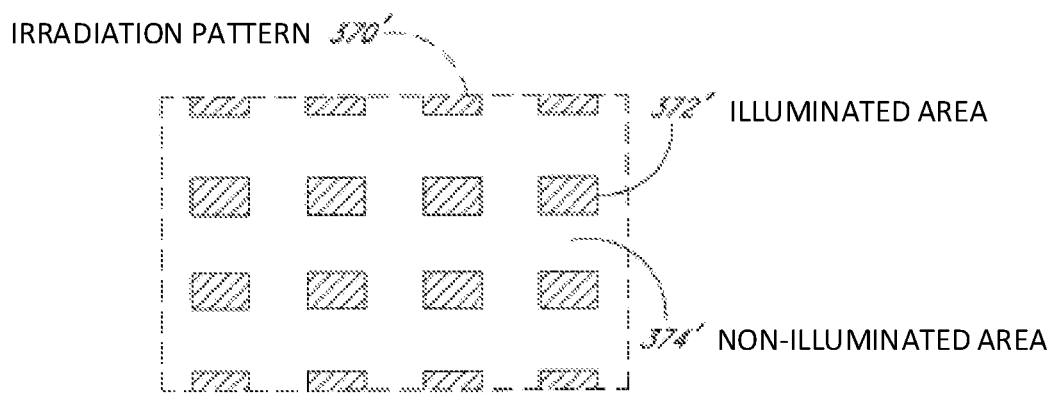

This selective irradiation can be used to reduce the thermal load on particular locations of the scalp 30 by moving the light from one illuminated area 372 to another. For example, by irradiating the scalp 30 with the irradiation pattern 370 schematically illustrated in FIG. 15A, the illuminated areas 372 of the scalp 30 are heated by interaction with the light, and the non-illuminated areas 374 are not heated. By subsequently irradiating the scalp 30 with the complementary irradiation pattern 370' schematically illustrated in FIG. 15B, the previously non-illuminated areas 374 are now illuminated areas 372', and the previously illuminated areas 372 are now non-illuminated areas 374'. A comparison of the illuminated areas 372 of the irradiation pattern 370 of FIG. 15A with the illuminated area 372' of the irradiation pattern 370' of FIG. 15B shows that the illuminated areas 372, 372' do not significantly overlap one another. In this way, the thermal load at the scalp 30 due to the absorption of the light can be distributed across the scalp 30, thereby avoiding unduly heating one or more portions of the scalp 30.

FIG. 16 schematically illustrates another therapy apparatus 400 in accordance with embodiments described herein. The therapy apparatus 400 comprises a plurality of light sources 410 in a housing 420. Each light source 410 has an output emission area positioned to irradiate a corresponding portion of the brain 20 with an efficacious power density and wavelength of light. In certain embodiments, these portions overlap such that the portion of the brain 20 irradiated by two or more light sources 410 overlap one another at least in part. As described herein, the light sources 410 can be activated by a controller (not shown) in concert or separately to produce a predetermined irradiation pattern.

The therapy apparatus 400 of FIG. 16 further comprises a cap 430 interposed between the light sources 410 and the patient's scalp 30, such that light passes through the cap 430 prior to reaching the scalp 30. In certain embodiments, the cap 430 is substantially optically transmissive at the wavelength and reduces back reflections of the light. The cap 430 of certain embodiments fits to the scalp 30 so as to substantially reduce air gaps between the scalp 30 and the cap 430. In certain embodiments, the cap 430 comprises a material having a refractive index which substantially matches a refractive index of the scalp 30. In certain embodiments, the cap 430 comprises a material having a refractive index which substantially matches a refractive index of the skin and/or hair of the scalp 30.

In the embodiment schematically illustrated by FIG. 16, the cap 430 is wearable over the patient's scalp 30. In certain such embodiments, the patient wears the cap 430 and is in a reclining position so as to place his head in proximity to the light sources 410. The cap 430 is adapted to inhibit temperature increases at the scalp 30 caused by the light from the light sources 410, as described herein (e.g., by cooling the scalp 30, by blanching a portion of the scalp 30, by diffusing the light prior to reaching the scalp 30).

Methods of Light Delivery

Preferred methods of phototherapy are based at least in part on the finding described above that, for a selected wavelength, the power density (light intensity or power per unit area, in $W/cm^2$) or the energy density (energy per unit area, in $J/cm^2$, or power density multiplied by the exposure time) of the light energy delivered to tissue is an important factor in determining the relative efficacy of the phototherapy, and efficacy is not as directly related to the total power or the total energy delivered to the tissue. In the methods described herein, power density or energy density as delivered to a portion of the patient's brain 20, which can include the area of infarct after a stroke, appears to be important factors in using phototherapy to treat and save surviving but endangered neurons in a zone of danger surrounding the infarcted area. Certain embodiments apply optimal power densities or energy densities to the intended target tissue, within acceptable margins of error.

In certain embodiments, the apparatus and methods of phototherapy described herein increase the cerebral blood flow of the patient. In certain such embodiments, the cerebral blood flow is increased by 10%, 15%, 20%, or 25% immediately post-irradiation, as compared to immediately prior to irradiation.

In certain embodiments, the apparatus and methods of phototherapy described herein are used to treat strokes or other sources of neurodegeneration. As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

As used herein, the term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

The term "cognitive function" as used herein refers to cognition and cognitive or mental processes or functions, including those relating to knowing, thinking, learning, perception, memory (including immediate, recent, or remote memory), and judging. Symptoms of loss of cognitive function can also include changes in personality, mood, and behavior of the patient. Diseases or conditions affecting cognitive function include Alzheimer's disease, dementia, AIDS or HIV infection, Cruetzfeldt-Jakob disease, head trauma (including single-event trauma and long-term trauma such as multiple concussions or other traumas which may result from athletic injury), Lewy body disease, Pick's disease, Parkinson's disease, Huntington's disease, drug or alcohol abuse, brain tumors, hydrocephalus, kidney or liver disease, stroke, depression, and other mental diseases which cause disruption in cognitive function, and neurodegeneration.

The term "motor function" as used herein refers to those bodily functions relating to muscular movements, primarily conscious muscular movements, including motor coordination, performance of simple and complex motor acts, and the like.

The term "neurologic function" as used herein includes both cognitive function and motor function.

The terms "cognitive enhancement" and "motor enhancement" as used herein refer to the improving or heightening of congnitive function and motor function, respectively.

The term "neurologic enhancement" as used herein includes both cognitive enhancement and motor enhancement.

As used herein, the term "neuroprotective-effective" as used herein refers to a characteristic of an amount of light energy, wherein the amount is a power density of the light energy measured in mW/cm$^2$. A neuroprotective-effective amount of light energy achieves the goal of preventing, avoiding, reducing, or eliminating neurodegeneration, which should result in cognitive enhancement and/or motor enhancement.

The term "neurologic function enhancement effective" as used herein refers to a characteristic of an amount of light energy, wherein the amount is a power density of the light energy measured in mW/cm$^2$. The amount of light energy achieves the goal of neuroprotection, motor enhancement, and/or cognitive enhancement.

Thus, a method for the treatment of stroke or for the enhancement of neurologic function in a patient in need of such treatment involves delivering a neurologic function enhancement effective amount or a neuroprotective-effective amount of light energy having a wavelength in the visible to near-infrared wavelength range to a target area of the patient's brain 20. In certain embodiments, the target area of the patient's brain 20 includes the area of infarct, i.e. to neurons within the "zone of danger." In other embodiments, the target area includes portions of the brain 20 not within the zone of danger. Without being bound by theory, it is believed that irradiation of healthy tissue in proximity to the zone of danger increases the production of ATP and copper ions in the healthy tissue and which then migrate to the injured cells within the region surrounding the infarct, thereby producing beneficial effects. Additional information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, which is incorporated in its entirety by reference herein.

In certain embodiments, delivering the neuroprotective amount of light energy includes selecting a surface power density of the light energy at the scalp 30 corresponding to the predetermined power density at the target area of the brain 20. As described above, light propagating through tissue is scattered and absorbed by the tissue. Calculations of the power density to be applied to the scalp 30 so as to deliver a predetermined power density to the selected target area of the brain 20 preferably take into account the attenuation of the light energy as it propagates through the skin and other tissues, such as bone and brain tissue. Factors known to affect the attenuation of light propagating to the brain 20 from the scalp 30 include, but are not limited to, skin pigmentation, the presence and color of hair over the area to be treated, amount of fat tissue, the presence of bruised tissue, skull thickness, and the location of the target area of the brain 20, particularly the depth of the area relative to the surface of the scalp 30. For example, to obtain a desired power density of 50 mW/cm$^2$ in the brain 20 at a depth of 3 cm below the surface of the scalp 30, phototherapy may utilize an applied power density of 500 mW/cm$^2$. The higher the level of skin pigmentation, the higher the power density applied to the scalp 30 to deliver a predetermined power density of light energy to a subsurface site of the brain 20.

In certain embodiments, treating a patient suffering from the effects of stroke comprises placing the therapy apparatus 10 in contact with the scalp 30 and adjacent the target area of the patient's brain 20. The target area of the patient's brain 20 can be previously identified such as by using standard medical imaging techniques. In certain embodiments, treatment further includes calculating a surface power density at the scalp 30 which corresponds to a preselected power density at the target area of the patient's brain 20. The calculation of certain embodiments includes factors that affect the penetration of the light energy and thus the power density at the target area. These factors include, but are not limited to, the thickness of the patient's skull, type of hair and hair coloration, skin coloration and pigmentation, patient's age, patient's gender, and the distance to the target area within the brain 20. The power density and other parameters of the applied light are then adjusted according to the results of the calculation.

The power density selected to be applied to the target area of the patient's brain 20 depends on a number of factors, including, but not limited to, the wavelength of the applied light, the type of CVA (ischemic or hemorrhagic), and the patient's clinical condition, including the extent of the affected brain area. The power density of light energy to be delivered to the target area of the patient's brain 20 may also be adjusted to be combined with any other therapeutic agent or agents, especially pharmaceutical neuroprotective agents, to achieve the desired biological effect. In such embodiments, the selected power density can also depend on the additional therapeutic agent or agents chosen.

In preferred embodiments, the treatment proceeds continuously for a period of about 10 seconds to about 2 hours, more preferably for a period of about 1 to about 10 minutes, and most preferably for a period of about 1 to 5 minutes. In other embodiments, the light energy is preferably delivered for at least one treatment period of at least about five minutes, and more preferably for at least one treatment period of at least ten minutes. The light energy can be pulsed during the treatment period or the light energy can be continuously applied during the treatment period.

In certain embodiments, the treatment may be terminated after one treatment period, while in other embodiments, the treatment may be repeated for at least two treatment periods. The time between subsequent treatment periods is preferably at least about five minutes, more preferably at least about 1 to 2 days, and most preferably at least about one week. In certain embodiments in which treatment is performed over the course of multiple days, the apparatus 10 is wearable over multiple concurrent days (e.g., embodiments of FIGS. 1, 3, 9A, 10, and 13). The length of treatment time and frequency of treatment periods can depend on several factors, including the functional recovery of the patient and the results of imaging analysis of the infarct. In certain embodiments, one or more treatment parameters can be adjusted in response to a feedback signal from a device (e.g., magnetic resonance imaging) monitoring the patient.

During the treatment, the light energy may be continuously provided, or it may be pulsed. If the light is pulsed, the pulses are preferably at least about 10 nanosecond long and occur at a frequency of up to about 100 kHz. Continuous wave light may also be used.

The thrombolytic therapies currently in use for treatment of stroke are typically begun within a few hours of the stroke. However, many hours often pass before a person who has suffered a stroke receives medical treatment, so the short time limit for initiating thrombolytic therapy excludes many patients from treatment. In contrast, phototherapy treatment of stroke appears to be more effective if treatment begins no earlier than several hours after the ischemic event has occurred. Consequently, the present methods of phototherapy may be used to treat a greater percentage of stroke patients.

In certain embodiments, a method provides a neuroprotective effect in a patient that had an ischemic event in the brain. The method comprises identifying a patient who has experienced an ischemic event in the brain. The method further comprises estimating the time of the ischemic event. The method further comprises commencing administration of a neuroprotective effective amount of light energy to the brain. The administration of the light energy is commenced no less than about two hours following the time of the ischemic event. In certain embodiments, phototherapy treatment can be efficaciously performed preferably within 24 hours after the ischemic event occurs, and more preferably no earlier than two hours following the ischemic event, still more preferably no earlier than three hours following the ischemic event, and most preferably no earlier than five hours following the ischemic event. In certain embodiments, one or more of the treatment parameters can be varied depending on the amount of time that has elapsed since the ischemic event.

Without being bound by theory, it is believed that the benefit in delaying treatment occurs because of the time needed for induction of ATP production, and/or the possible induction of angiogenesis in the region surrounding the infarct. Thus, in accordance with one preferred embodiment, the phototherapy for the treatment of stroke occurs preferably about 6 to 24 hours after the onset of stroke symptoms, more preferably about 12 to 24 hours after the onset of symptoms. It is believed, however, that if treatment begins after about 2 days, its effectiveness will be greatly reduced.

In certain embodiments, the phototherapy is combined with other types of treatments for an improved therapeutic effect. Treatment can comprise directing light through the scalp of the patient to a target area of the brain concurrently with applying an electromagnetic field to the brain. In such embodiments, the light has an efficacious power density at the target area and the electromagnetic field has an efficacious field strength. For example, the apparatus 50 can also include systems for electromagnetic treatment, e.g., as described in U.S. Pat. No. 6,042,531 issued to Holcomb, which is incorporated in its entirety by reference herein. In certain embodiments, the electromagnetic field comprises a magnetic field, while in other embodiments, the electromagnetic field comprises a radio-frequency (RF) field. As another example, treatment can comprise directing an efficacious power density of light through the scalp of the patient to a target area of the brain concurrently with applying an efficacious amount of ultrasonic energy to the brain. Such a system can include systems for ultrasonic treatment, e.g., as described in U.S. Pat. No. 5,054,470 issued to Fry et al., which is incorporated in its entirety by reference herein.

Phototherapy Examples

EXAMPLE 1

An in vitro experiment was done to demonstrate one effect of phototherapy on neurons, namely the effect on ATP production. Normal Human Neural Progenitor (NHNP) cells were obtained cryopreserved through Clonetics of Baltimore, Md., catalog #CC-2599. The NHNP cells were thawed and cultured on polyethyleneimine (PEI) with reagents provided with the cells, following the manufacturers' instructions. The cells were plated into 96 well plates (black plastic with clear bottoms, Becton Dickinson of Franklin Lakes, N.J.) as spheroids and allowed to differentiate into mature neurons over a period of two weeks.

A Photo Dosing Assembly (PDA) was used to provide precisely metered doses of laser light to the NHNP cells in the 96 well plates. The PDA included a Nikon Diaphot inverted microscope (Nikon of Melville, N.Y.) with a LUDL motorized x,y,z stage (Ludl Electronic Products of Hawthorne, N.Y.). An 808 nanometer laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 millimeter diameter circle when it reached the bottom of the 96 well plates. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nanometer laser light on the NHNP cells. The first was the CellTiter-Glo Luminescent Cell Viability Assay (Promega of Madison, Wis.). This assay generates a "glowtype" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems of Sunnyvale, Calif.). Amounts of ATP present in the NHNP cells were quantified in Relative Luminescent Units (RLUs) by the luminometer.

The second assay used was the alamarBlue assay (Biosource of Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. Laser irradiation is also thought to have an effect on these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices of Sunnyvale, Calif.) was used to measure the absorbance of a well containing NHNP cells, media and alamarBlue diluted 10% v/v. The absorbance of each well was measured at 570 nanometers and 600 nanometers and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nanometers. For the CellTiter-Glo assay, 20 wells were lased for 1 second and compared to an unlased control group of 20 wells. The CellTiter-Glo reagent was added 10 minutes after lasing completed and the plate was read after the cells had lysed and the luciferase reaction had stabilized. The average RLUs measured for the control wells was 3808+/−3394 while the laser group showed a two-fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the two-fold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Wells from the same plate can still be compared though, since plating conditions were identical. The alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). These alamarBlue results support the earlier findings in that they show a similar positive effect of the laser treatment on the cells.

Increases in cellular ATP concentration and a more reduced state within the cell are both related to cellular metabolism and are considered to be indications that the cell is viable and healthy. These results are novel and significant in that they show the positive effects of laser irradiation on cellular metabolism in in-vitro neuronal cell cultures.

EXAMPLE 2

In a second example, transcranial laser therapy was investigated using a low-energy infrared laser to treat behavioral deficits in a rabbit small clot embolic stroke model (RSCEM). This example is described in more detail by P. A. Lapchak et al., "*Transcranial Infrared Laser Therapy Improves Clinical Rating Scores After Embolic Strokes in Rabbits,*" Stroke, Vol. 35, pp. 1985-1988 (2004), which is incorporated in its entirety by reference herein.

RSCEM was produced by injection of blood clots into the cerebral vasculature of anethestized male New Zealand White rabbits, resulting in ischemia-induced behavioral deficits that can be measured quantitatively with a dichotomous rating scale. In the absence of treatment, small numbers of microclots caused no grossly apparent neurologic dysfunction while large numbers of microclots invariably caused encephalopathy or death. Behaviorally normal rabbits did not have any signs of impairment, whereas behaviorally abnormal rabbits had loss of balance, head leans, circling, seizure-type activity, or limb paralysis.

For laser treatment, a laser probe was placed in direct contact with the skin. The laser probe comprised a low-energy laser (wavelength of 808±5 nanometers) fitted with an OZ Optics Ltd. fiber-optic cable and a laser probe with a diameter of approximately 2 centimeters. Instrument design studies showed that these specifications would allow for laser penetration of the rabbit skull and brain to a depth of 2.5 to 3 centimeters, and that the laser beam would encompass the majority of the brain if placed on the skin surface posterior to bregma on the midline. Although the surface skin temperature below the probe was elevated by up to 3° C., the focal brain temperature directly under the laser probe was increased by 0.8° C. to 1.8° C. during the 10-minute laser treatment using the 25 mW/cm$^2$ energy setting. Focal brain temperature returned to normal within 60 minutes of laser treatment.

The quantitative relationship between clot dose and behavioral or neurological deficits was evaluated using logistic (S-shaped) curves fitted by computer to the quantal dose-response data. These parameters are measures of the amount of microclots (in mg) that produced neurologic dysfunction in 50% of a group of animals ($P_{50}$). A separate curve was generated for each treatment condition, with a statistically significant increase in the $P_{50}$ value compared with control being indicative of a behavioral improvement. The data were analyzed using the t test, which included the Bonferroni correction when appropriate.

To determine if laser treatment altered physiological variables, 14 rabbits were randomly divided into 2 groups, a control group and a laser-treated group (25 mW/cm$^2$ for 10 minutes). Blood glucose levels were measured for all embolized rabbits using a Bayer Elite XL 3901B Glucometer, and body temperature was measured using a Braun Thermoscan Type 6013 digital thermometer. Within 60 minutes of embolization, there was an increase in blood glucose levels in both the control group and the laser-treated group that was maintained for the 2 hours post-embolization observation time. Blood glucose levels returned to control levels by 24 hours, regardless of the extent of stroke-induced behavioral deficits. Laser treatment did not significantly affect glucose levels at any time. Neither embolization nor laser treatment significantly affected body temperature in either group of rabbits.

Figure 17A:
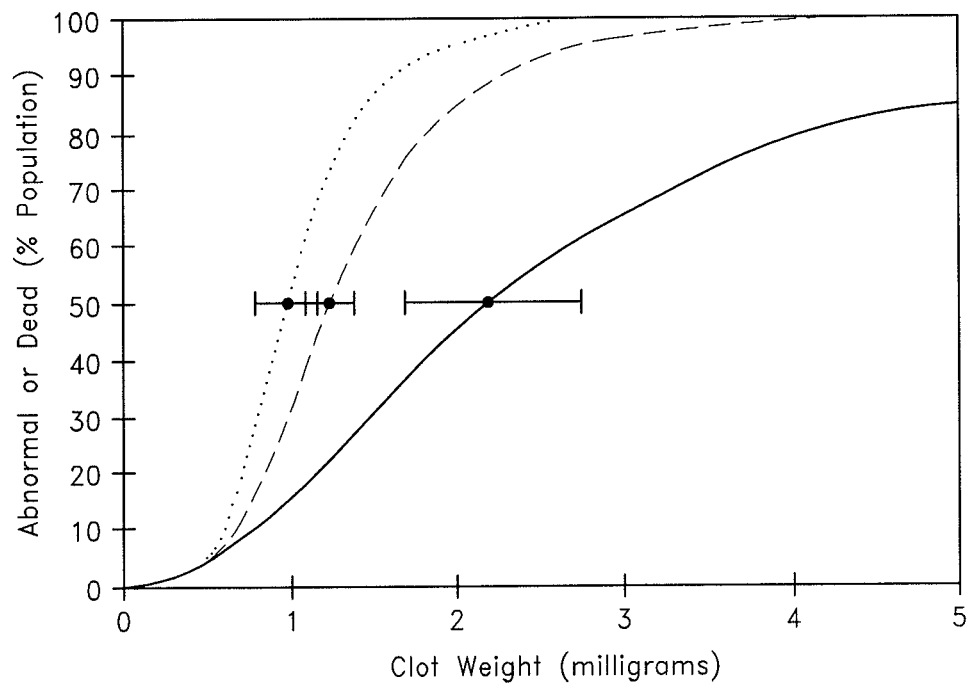
FIG. 17A is a graph of the effects of laser treatment of 7.5 mW/cm$^2$ for a treatment duration of 2 minutes on a population of rabbits having small clot embolic stroke.

FIG. 17A is a graph for the percentage of the population which was either abnormal or dead as a function of the clot weight in milligrams for laser treatment of 7.5 mW/cm$^2$ for a treatment duration of 2 minutes. As shown by FIG. 17A, the control curve (dotted line) has a $P_{50}$ value of 0.97±0.19 mg (n=23). Such laser treatment initiated 3 hours after the stroke significantly improved behavioral performance, with the $P_{50}$ value increased to 2.21±0.54 mg (n=28, *P=0/05) (solid line). The effect was durable and was measurable 3 weeks after embolization. However, the same setting did not improve behavior if there was a long delay (24 hours) after embolization (dashed line) ($P_{50}$=1.23±0.15 mg, n=32).

Figure 17B:
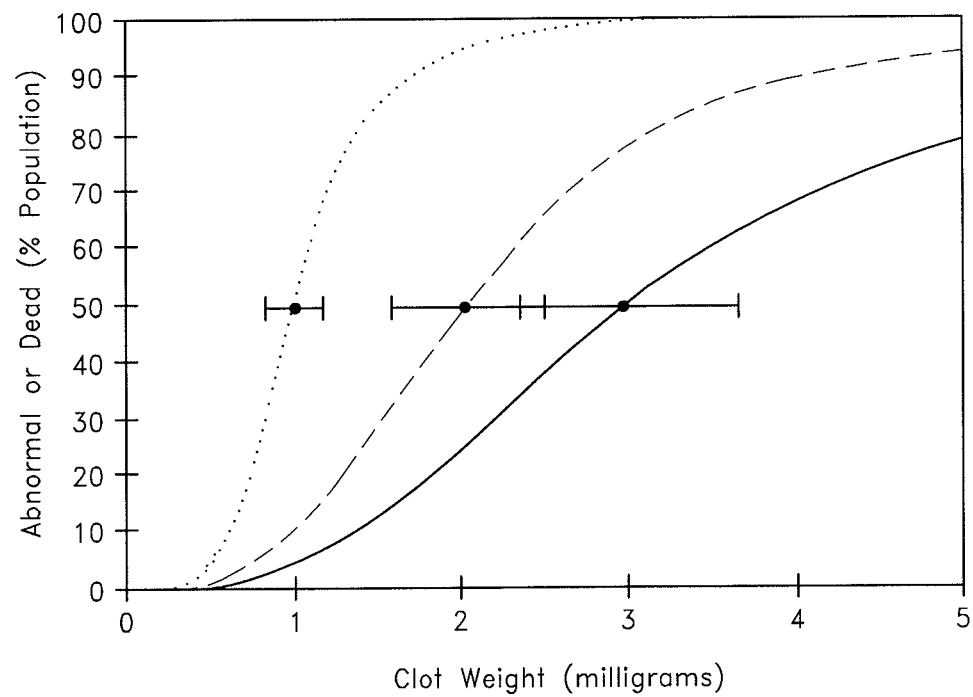
FIG. 17B is a graph of the effects of laser treatment of 25 mW/cm$^2$ for a treatment duration of 10 minutes on a population of rabbits having small clot embolic stroke.

FIG. 17B is a graph for the percentage of the population which was either abnormal or dead as a function of the clot weight in milligrams for laser treatment of 25 mW/cm2 for a treatment duration of 10 minutes. As shown by FIG. 17B, the control curve (dotted line) has a $P_{50}$ value of 1.10±0.17 mg (n=27). Such laser treatment initiated 1 (dashed line) or 6 (solid line) hours after embolization also significantly increased behavioral performance, with the $P_{50}$ value increased to 2.02±0.46 mg (n=18, *P<0.05) and 2.98±0.65 mg (n=26, *P<0.05), respectively.

Figure 18:
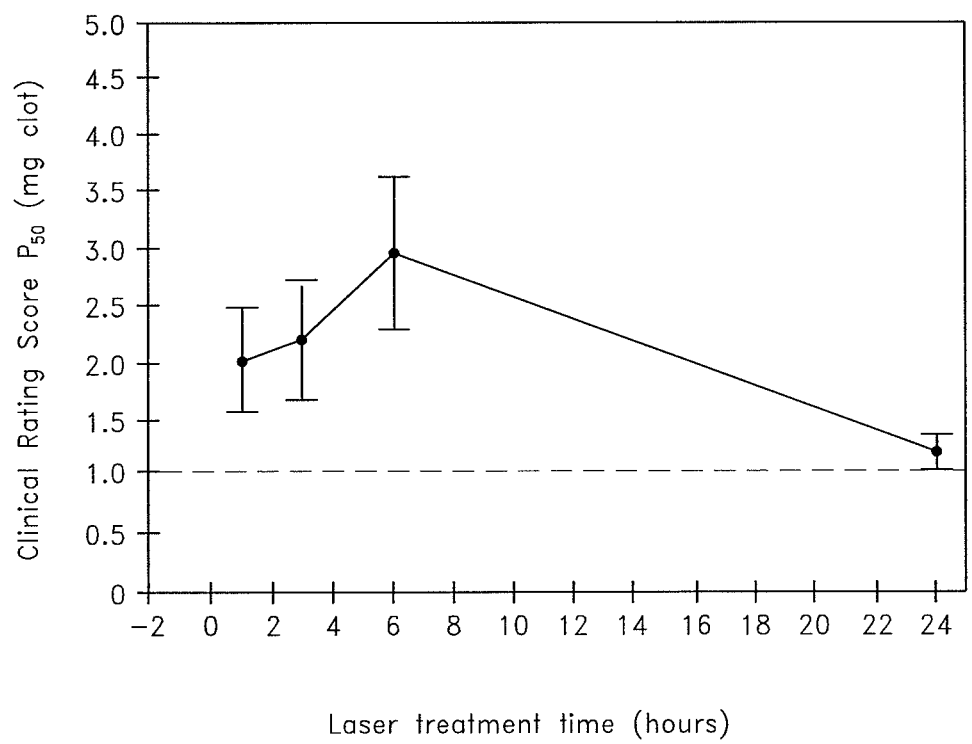
FIG. 18 is a graph showing the therapeutic window for laser-induced behavioral improvements after small-clot embolic strokes in rabbits.

FIG. 18 is a graph showing the therapeutic window for laser-induced behavioral improvements after small-clot embolic strokes in rabbits. Results are shown as clinical rating score $P_{50}$ (mg clot) given as mean±SEM for the number of rabbits per time point (number in brackets) for laser treatment initiated 1, 3, 6, or 24 hours after embolization as shown on the x-axis. The horizontal line represents the mean of the control $P_{50}$ values (*P<0.05).

The results in the RSCEM showed that laser treatment significantly improved behavioral rating scores after embolic strokes in rabbits without affecting body temperature and blood glucose levels. In addition, laser treatment was effective when initiated up to 6 hours after strokes, which is later than any other previously effective single therapy in the same preclinical stroke model. Moreover, the effect was durable and was measurable up to 21 days after embolization. The magnitudes of laser-induced improvement in rabbits are similar to previously tested thrombollytics (alteplase, tenecteplase, and microplasmin) and neuroprotective compounds (NXY-059), which are undergoing clinical development.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method of treating an ischemic stroke in a subject, the method comprising:
    fitting, onto a scalp of the subject, a light therapy apparatus comprising: (i) a light source, (ii) a temperature sensor, and (iii) an element interposed between the light source and the scalp such that a first side of the element faces the scalp and a second side of the element faces the light source,
    wherein the first side of the element includes: (i) first portions that contact portions of the scalp and (ii) second portions that are spaced away from the scalp;
    applying, via the first portions of the first side of the element, pressure to compress the portions of the scalp and force blood out therefrom;
    irradiating, using the light source, a portion of a brain of the subject at a depth of 2 centimeters below a dura of the subject with a peak power density between 0.01 mW/cm² and 100 mW/cm² and a wavelength of light in the visible to near-infrared wavelength range;
    detecting, using the temperature sensor, a scalp temperature of the subject during the irradiating; and
    adjusting, during the irradiating, a parameter of the light source based on the detected scalp temperature to maintain the scalp temperature below a predetermined level,
    wherein the treating occurs within 24 hours of the subject experiencing the ischemic stroke.

2. The method of claim 1, wherein the light source comprises a low-energy laser.

3. The method of claim 1, wherein the light has a wavelength between 630 nanometers and 1064 nanometers.

4. The method of claim 3, wherein the light has a wavelength between 803 and 813 nanometers.

5. The method of claim 1, wherein the peak power density is between 0.01 mW/cm² and 50 mW/cm².

6. The method of claim 1, wherein the peak power density is between 2 mW/cm² and 20 mW/cm².

7. The method of claim 1, wherein a cortical cerebral blood flow of the subject is increased by 10%, 15%, 20%, or 25% immediately post-irradiation, as compared to immediately prior to irradiation.

8. The method of claim 1, wherein the element applies pressure to compress at least a portion of the scalp of the subject, thereby blanching the portion of the scalp and decreasing absorption of the light by blood in the scalp.

9. The method of claim 1, wherein at least a portion of the element is within an optical path of light from the light source to the scalp of the subject.

10. The method of claim 9, wherein the element is optically transmissive at the wavelength of light from the light source.

11. The method of claim 9, wherein the element comprises a material having a refractive index which matches a refractive index of the scalp of the subject.

12. The method of claim 1, wherein the element comprises a conduit containing a coolant which flows through the conduit toward the scalp of the subject, is heated by the scalp of the subject, and flows away from the scalp of the subject.

13. The method of claim 1, wherein treating the subject with a light source results in a temperature increase at the scalp of the subject by up to 3° C.

14. A method of treating a source of neurodegeneration in a subject, the method comprising:
    fitting, onto a scalp of the subject, a light therapy apparatus comprising: (i) a light source, (ii) a temperature sensor, and (iii) an element interposed between the light source and the scalp such that a first side of the element faces the scalp and a second side of the element faces the light source,
    wherein the first side of the element includes: (i) first portions that contact portions of the scalp and (ii) second portions that are spaced away from the scalp;
    applying, via the first portions of the first side of the element, pressure to compress the portions of the scalp to force blood out therefrom;
    irradiating, using the light source, a portion of a brain of the subject at a depth of 2 centimeters below a dura of the subject with a peak power density between 0.01 mW/cm² and 100 mW/cm² and a wavelength of light in the visible to near-infrared wavelength range;
    detecting, using a temperature sensor, a scalp temperature of the subject during the irradiating; and
    adjusting, during the irradiating, a parameter of the light source based on the detected scalp temperature to maintain the scalp temperature below a predetermined level.

15. The method of claim 1, wherein the light is applied continuously.

16. The method of claim 1, wherein the light is pulsed.

17. The method of claim 16, wherein the light has a pulsed frequency of up to 100 kHz.

18. The method of claim 14, wherein the light has a wavelength between 630 nanometers and 1064 nanometers.

19. The method of claim 14, wherein the light is applied continuously.

20. The method of claim 14, wherein the light is pulsed.

21. The method of claim 20, wherein the light has a pulsed frequency of up to 100 kHz.

22. The method of claim 14, wherein the element applies pressure to compress at least a portion of the scalp of the subject, thereby blanching the portion of the scalp and decreasing absorption of the light by blood in the scalp.

23. The method of claim 14, wherein the element comprises a conduit containing a coolant which flows through the conduit toward the scalp of the subject, is heated by the scalp of the subject, and flows away from the scalp of the subject.

24. The method of claim 1, wherein the element reduces temperature increases at the scalp of the subject.

25. The method of claim 14, wherein the element reduces temperature increases at the scalp of the subject.

* * * * *